US010259765B2

(12) United States Patent
Dakka et al.

(10) Patent No.: US 10,259,765 B2
(45) Date of Patent: Apr. 16, 2019

(54) PROCESS FOR MAKING CYCLOHEXANONE

(71) Applicant: ExxonMobil Chemical Patents Inc., Baytown, TX (US)

(72) Inventors: Jihad M. Dakka, Whitehouse Station, NJ (US); Ashley J. Malik, Houston, TX (US); Christopher L. Becker, Manhattan, KS (US); Jason D. Davis, Zachary, LA (US); Kirk C. Nadler, Houston, TX (US); Jose M. Vargas, Friendswood, TX (US); Tan-Jen Chen, Seattle, WA (US); Seth M. Washburn, Houston, TX (US); Jörg F. W. Weber, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/743,367

(22) PCT Filed: Jun. 17, 2016

(86) PCT No.: PCT/US2016/038035
§ 371 (c)(1),
(2) Date: Jan. 10, 2018

(87) PCT Pub. No.: WO2017/023430
PCT Pub. Date: Feb. 9, 2017

(65) Prior Publication Data
US 2018/0194705 A1 Jul. 12, 2018

Related U.S. Application Data

(60) Provisional application No. 62/199,784, filed on Jul. 31, 2015.

(51) Int. Cl.
| | |
|---|---|
| *C07C 45/00* | (2006.01) |
| *C07C 2/74* | (2006.01) |
| *C07C 407/00* | (2006.01) |
| *B01J 23/96* | (2006.01) |
| *B01J 38/04* | (2006.01) |
| *B01J 38/06* | (2006.01) |
| *B01J 38/12* | (2006.01) |
| *B01J 38/52* | (2006.01) |
| *B01J 38/56* | (2006.01) |
| *B01J 23/44* | (2006.01) |
| *B01J 35/00* | (2006.01) |
| *B01J 8/06* | (2006.01) |
| *B01J 38/10* | (2006.01) |
| *B01J 38/50* | (2006.01) |
| *B01J 38/64* | (2006.01) |
| *C07C 49/403* | (2006.01) |

(Continued)

(52) U.S. Cl.
CPC ............... *C07C 45/006* (2013.01); *B01J 8/06* (2013.01); *B01J 23/44* (2013.01); *B01J 23/96* (2013.01); *B01J 35/008* (2013.01); *B01J 38/04* (2013.01); *B01J 38/06* (2013.01); *B01J 38/10* (2013.01); *B01J 38/12* (2013.01); *B01J 38/50* (2013.01); *B01J 38/52* (2013.01); *B01J 38/56* (2013.01); *B01J 38/64* (2013.01); *C07C 49/403* (2013.01); *B01J 23/58* (2013.01); *B01J 2219/00081* (2013.01); *B01J 2219/00162* (2013.01); *C07C 2/74* (2013.01); *C07C 37/001* (2013.01); *C07C 407/00* (2013.01); *C07C 2601/14* (2017.05); *Y02P 20/584* (2015.11)

(58) Field of Classification Search
CPC .......... C07C 45/06; C07C 2/74; C07C 407/00
See application file for complete search history.

(56) References Cited

U.S. PATENT DOCUMENTS

| | | |
|---|---|---|
| 3,076,810 A | 2/1963 | Duggan et al. |
| 3,322,651 A | 5/1967 | Nielsen et al. |
| 3,998,884 A | 12/1976 | Gibson |

(Continued)

FOREIGN PATENT DOCUMENTS

| | | | | |
|---|---|---|---|---|
| DE | 19 52 208 A | 4/1971 | | |
| DE | 1952208 A1 * | 4/1971 | ........... | C07C 45/006 |

(Continued)

OTHER PUBLICATIONS

Dimian, A.C., et al, "Phenol Hydrogenation to Cyclohexanone", Chemical Process Design: Computer-Aided Case Studies, pp. 129-172, 2008.

(Continued)

*Primary Examiner* — Sikarl A Witherspoon

(57) ABSTRACT

Disclosed are novel processes for making cyclohexanone compositions, from a mixture comprising phenol, cyclohexanone, and cyclohexylbenzene. The process includes hydrogenation of a feed stream comprising phenol, cyclohexanone, and cyclohexylbenzene. The feed stream may be subjected to one or more pre-hydrogenation treatments, such as passing through one or more sorbents, addition of basic chemical agents, and/or addition of water, so as to improve catalyst activity, minimize undesired side reactions, and/or remove catalyst poisons from the feed stream. The feed stream may be provided to a hydrogenation reaction zone in the vapor phase, with periodic alterations to hydrogenation reaction conditions such that the feed is provided in mixed liquid and vapor phase in order to carry out liquid washing of a hydrogenation catalyst bed within the hydrogenation reaction zone.

19 Claims, 12 Drawing Sheets

(51) Int. Cl.
    *B01J 23/58* (2006.01)
    *C07C 37/00* (2006.01)

(56) References Cited

U.S. PATENT DOCUMENTS

| | | |
|---|---|---|
| 4,021,490 A | 5/1977 | Hudson |
| 4,200,553 A | 4/1980 | Van Peppen et al. |
| 4,203,923 A | 5/1980 | Yeh et al. |
| 5,064,507 A | 11/1991 | O'Donnell et al. |
| 5,168,983 A | 12/1992 | Tan et al. |
| 6,015,927 A | 1/2000 | Kiel |
| 6,037,513 A | 3/2000 | Chang et al. |
| 6,215,028 B1 | 4/2001 | Oster et al. |
| 6,730,625 B1 | 4/2004 | Chang et al. |
| 7,199,271 B2 | 4/2007 | Fodor |
| 7,579,506 B2 | 8/2009 | Leconte et al. |
| 8,222,459 B2 | 7/2012 | Dakka et al. |
| 8,389,773 B2 | 3/2013 | Parton et al. |
| 8,618,334 B2 | 12/2013 | Horsels et al. |
| 8,772,550 B2 | 7/2014 | Parton et al. |
| 8,802,897 B2 | 8/2014 | Neumann et al. |
| 8,921,603 B2 | 12/2014 | Kuechler et al. |
| 2012/0323042 A1 | 12/2012 | Parton et al. |
| 2017/0152201 A1 | 6/2017 | Becker et al. |
| 2017/0204033 A1 | 7/2017 | Becker et al. |
| 2017/0204034 A1 | 7/2017 | Becker et al. |
| 2017/0204035 A1 | 7/2017 | Becker et al. |
| 2017/0204037 A1 | 7/2017 | Becker et al. |
| 2017/0275226 A1 | 9/2017 | Kuechler et al. |
| 2017/0283353 A1 | 10/2017 | Becker et al. |

FOREIGN PATENT DOCUMENTS

| | | |
|---|---|---|
| EP | 0 606 553 A | 7/1994 |
| EP | 1 575 892 B | 9/2005 |
| GB | 1257607 A | 12/1971 |
| GB | 1 332 211 A | 10/1973 |
| JP | 4342156 B | 10/2009 |
| WO | 2009/131769 A | 10/2009 |
| WO | 2009/134514 A | 11/2009 |
| WO | 2010/098916 A | 9/2010 |
| WO | 2012/036819 A | 3/2012 |
| WO | 2012/036820 A | 3/2012 |
| WO | 2012/036822 A | 3/2012 |
| WO | 2012/036823 A | 3/2012 |
| WO | 2012/036828 A | 3/2012 |
| WO | 2012/036830 A | 3/2012 |
| WO | 2014/137624 A | 9/2014 |
| WO | 2016/025219 A | 2/2016 |
| WO | 2016/053466 A | 4/2016 |
| WO | 2017/019196 A | 2/2017 |
| WO | 2017/023429 A | 2/2017 |

OTHER PUBLICATIONS

Díaz, E., et al., "Hydrogenation of phenol in aqueous phase with palladium on activated carbon catalysts", Chemical Engineering Journal, vol. 131, pp. 65-71, 2007.

Gonzalez-Velasco, J.R., et al., "Activity and selectivity of palladium catalysts during the liquid-phase hydrogenation of phenol. Influence of temperature and pressure", Industrial & Engineering Chemical Research, vol. 34, No. 4, pp. 1031-1036, 1995.

Van Peppen, J.F. et al., "Phenol Hydrogenation Process", Catalysis of Organic Reactions, pp. 355-372, 1985.

\* cited by examiner

PROCESS FOR MAKING CYCLOHEXANONE

PRIORITY CLAIM

This application is a National Phase Application claiming priority to PCT Application Serial No. PCT/US2016/038035 filed Jun. 17, 2016, and U.S. Provisional Application Ser. No. 62/199,784 filed Jul. 31, 2015, the disclosures of which are fully incorporated herein by their reference.

CROSS-REFERENCE TO RELATED APPLICATIONS

This application is related to U.S. Provisional Application Ser. No. 62/199,768 filed Jul. 31, 2015 (2015EM199); U.S. Provisional Application No. 62/198,470 filed Jul. 29, 2015 (2015EM194); U.S. Provisional Application Ser. No. 62/140,702 filed Mar. 31, 2015 (2015EM074); U.S. Provisional Application Ser. No. 62/057,919 filed Sep. 30, 2014 (2014EM262); and European Application No. 15151424.7 filed Jan. 16, 2015, the disclosures of which are fully incorporated herein by their reference.

FIELD

The present invention relates to processes for making cyclohexanone. In particular, the present invention relates to processes for making cyclohexanone by phenol hydrogenation. The present invention is useful, e.g., in making cyclohexanone from cyclohexylbenzene oxidation and cyclohexylbenzene hydroperoxide cleavage.

BACKGROUND

Cyclohexanone is an important material in the chemical industry and is widely used in, for example, production of phenolic resins, bisphenol A, ε-caprolactam, adipic acid, and plasticizers. One method for making cyclohexanone is by hydrogenating phenol.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. The separated phenol product can then be converted to cyclohexanone by a step of hydrogenation.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide, which can then be cleaved to produce a cleavage mixture of phenol and cyclohexanone, which, in turn, can be separated to obtain pure, substantially equimolar phenol and cyclohexanone products. This cyclohexylbenzene-based process for co-producing phenol and cyclohexanone can be highly efficient in making these two important industrial materials. Given the higher commercial value of cyclohexanone than phenol, it is highly desirable that in this process more cyclohexanone than phenol be produced. While this can be achieved by subsequently hydrogenating the pure phenol product produced in this process to convert a part or all of the phenol to cyclohexanone, a more economical process and system would be highly desirable.

One solution to making more cyclohexanone than phenol from the above cyclohexylbenzene-based process is to hydrogenate a mixture containing phenol and cyclohexanone obtained from the cleavage mixture to convert at least a portion of the phenol contained therein to cyclohexanone. However, because the phenol/cyclohexanone mixture invariably contains non-negligible amounts of (i) catalyst poison component(s) (such as S-containing components) that can poison the hydrogenation catalyst, and (ii) cyclohexylbenzene that can be converted into bicyclohexane in the hydrogenation step, and because hydrogenation of the phenol/cyclohexanone/cyclohexylbenzene mixture can also lead to the formation of cyclohexanol, resulting in yield loss, this process is not without challenge. In short, the unconventional feed to a phenol hydrogenation process, produced by the aforementioned route including hydroalkylation of benzene, presents a great deal of challenges to maintaining the desired activity of phenol hydrogenation catalyst, and the desired selectivity to cyclohexanone.

Some references of potential interest in this regard may include: U.S. Pat. Nos. 3,076,810; 3,322,651; 3,998,884; 4,021,490; 4,200,553; 4,203,923; 4,439,409; 4,826,667; 4,954,325; 5,064,507; 5,168,983; 5,236,575; 5,250,277; 5,362,697; 6,015,927; 6,037,513; 6,046,365; 6,077,498; 6,215,028; 6,730,625; 6,756,030; 7,199,271; 7,579,506; 7,579,511; 8,222,459; 8,389,773; 8,618,334; 8,772,550; 8,802,897; and 8,921,603. Other references of potential interest include WIPO Publication Nos. WO 97/17290; WO 2009/128984; WO 2009/131769; WO 2009/134514; WO 2010/098916; WO 2012/036820; WO 2012/036822; WO 2012/036823; WO 2012/036828; WO 2012/036830; and WO 2014/137624. Further references of potential interest include EP 0 293 032; EP 0 606 553; EP 1 575 892; JP 434156 B2; as well as Alexandre C. Dimian and Costin Sorin Bildea, *Chemical Process Design: Computer-Aided Case Studies*, pp. 129-172 (Wiley, 2008); Van Peppen, J. F. et al., *Phenol Hydrogenation Process*, in Catalysis of Organic Reactions, pp. 355-372 (1985, ed. R. L. Augustine); Díaz et al., *Hydrogenation of phenol in aqueous phase with palladium on activated carbon catalysts*, CHEM. ENG'G J. 131 (2007) at 65-71; and Gonzalez-Velazco et al., *Activity and selectivity of palladium catalysts during the liquid-phase hydrogenation of phenol [to cyclohexanone (CHXN)]. Influence of temperature and pressure*, INDUSTRIAL & ENG'G CHEM. RESEARCH (April 1995), Vol. 34, No. 4, p. 1031.

SUMMARY

The present invention addresses various problems presented by the mixed feed to phenol hydrogenation indicated above. Methods according to some aspects include subjecting the hydrogenation feed (comprising phenol, cyclohexanone, and cyclohexylbenzene) to one or more pre-hydrogenation treatments, such as (i) contacting the first middle effluent with one or more posterior sorbents; (ii) contacting the first middle effluent with one or more posterior distillation columns; (iii) adding to the first middle effluent a basic chemical agent selected from the group consisting of amines, inorganic bases, and mixtures thereof; and (iv) adding water to the first middle effluent such that water is present in the hydrogenation feed in an amount ranging from 0.1 wt % to 20 wt %, based on the weight of the hydrogenation feed.

Methods according to further aspects include, during a first period of time, continuously providing hydrogen, the hydrogenation feed, and a catalyst inhibitor to a hydrogenation reaction zone with a hydrogenation catalyst disposed therein, so as to inhibit the activity of the catalyst; ceasing the provision of the catalyst inhibitor to the hydrogenation reaction zone; and thereafter, during a second period of time subsequent to the first period of time, continuing to provide hydrogen and the hydrogenation feed to the hydrogenation reaction zone. Such temporary provision of catalyst inhibitor may be useful in preventing catalyst over-activity, e.g., during start-up with fresh catalyst.

Methods according to yet further aspects include reducing the partial pressure of the hydrogen in the hydrogenation reaction zone (e.g., by providing an inert fluid with the hydrogen to the hydrogenation reaction zone).

Methods according to other aspects include continuously providing hydrogen and hydrogenation feed comprising phenol, cyclohexanone, and cyclohexylbenzene to a hydrogenation reaction zone in which a hydrogenation catalyst bed is disposed, thereby maintaining a reaction medium flowing through the hydrogenation catalyst bed within the hydrogenation reaction zone; and maintaining temperature and pressure in the hydrogenation reaction zone such that the reaction medium flowing through the hydrogenation catalyst bed remains in mixed liquid and vapor phase. Maintaining such mixed-phase conditions allows liquid to flow through the catalyst bed, which may act to remove impurities that would otherwise accumulate on the catalyst.

In yet further aspects, the mixed-phase operation may be a temporary departure from standard operating conditions in either vapor or liquid phase, preferably in vapor phase. Such embodiments may include: (a) during a first period of time, flowing (i) hydrogen and (ii) a vapor-phase hydrogenation feed comprising phenol, cyclohexanone, and cyclohexylbenzene through a hydrogenation catalyst bed so as to hydrogenate at least a portion of the phenol in the vapor-phase hydrogenation feed to cyclohexanone, and further so as to form one or more hydrocarbon and/or oxygenate impurities that adsorb or absorb onto at least a portion of the hydrogenation catalyst bed; and (b) during a second period of time subsequent to the first period of time, flowing (i) hydrogen and (ii) a mixed liquid- and vapor-phase hydrogenation feed comprising phenol, cyclohexanone, and cyclohexylbenzene through the hydrogenation catalyst bed so as to hydrogenate at least a portion of the phenol in the mixed liquid- and vapor-phase hydrogenation feed to cyclohexanone, and further so as to remove at least a portion of the one or more hydrocarbon and/or oxygenate impurities from the hydrogenation catalyst bed. In such embodiments, the temporary mixed-phase provides a temporary liquid wash to the hydrogenation catalyst bed, thereby removing any impurities that have accumulated, preferably restoring at least some activity to the catalyst that had been lost due to the impurities. Flowing mixed-phase hydrogenation feed during the second period of time may be accomplished by adjusting temperature and/or pressure hydrogenation reaction conditions maintained during the first period of time (in which vapor-phase hydrogenation feed is flowed through the catalyst bed) so as to obtain conditions suitable for the mixed-phase washing.

DETAILED DESCRIPTION

Figure 1:
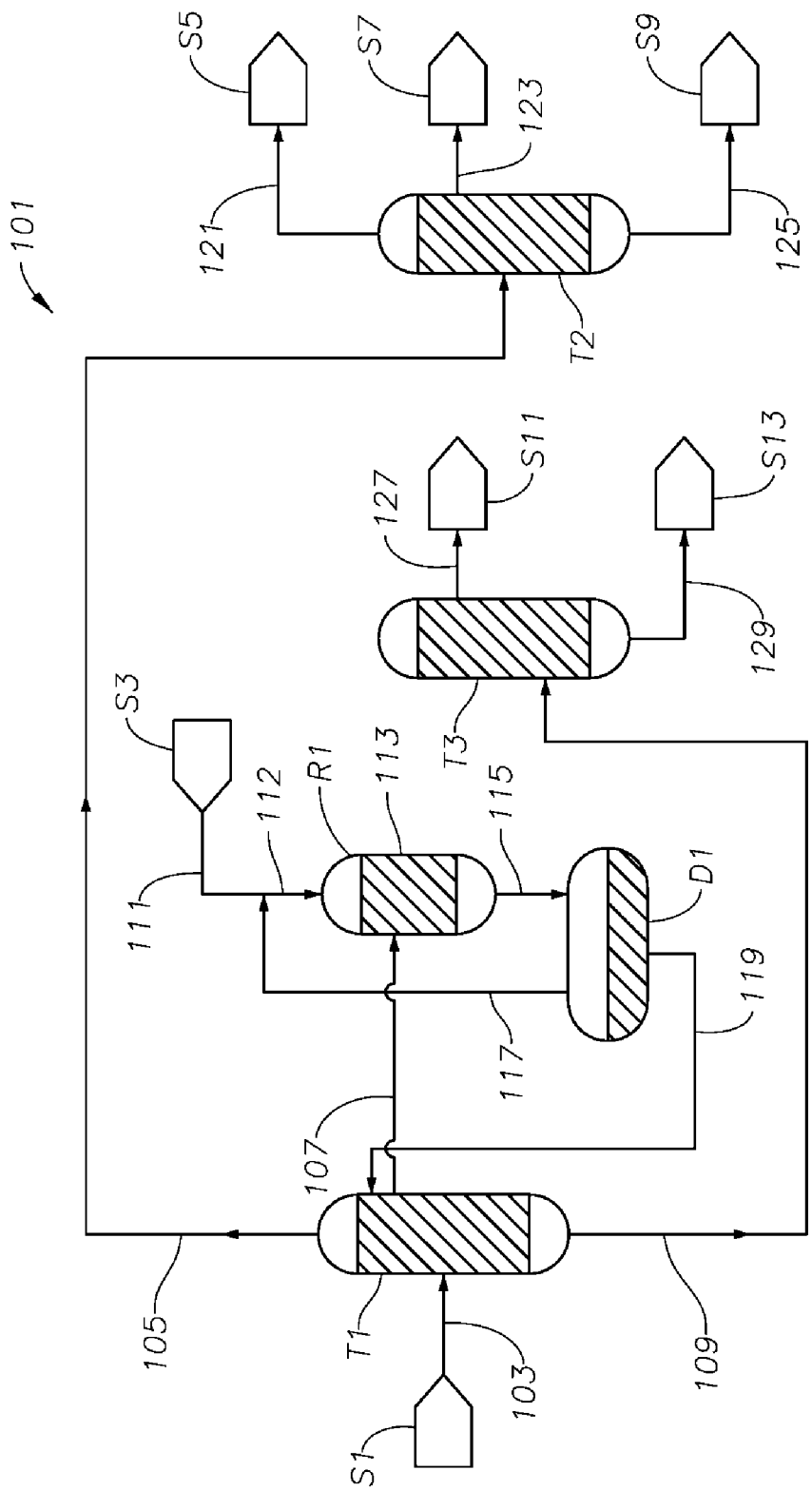
FIG. 1 is a schematic diagram showing a process/system for making cyclohexanone from a first mixture comprising phenol, cyclohexanone and cyclohexylbenzene including a first distillation column T1, a hydrogenation reactor R1, and a cyclohexanone purification column T2.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments comprising "a light component" include embodiments where one, two or more light components exist, unless specified to the contrary or the context clearly indicates that only one light component exists.

A "complex" as used herein means a material formed by identified components via chemical bonds, hydrogen bonds, and/or physical forces.

An "operation temperature" of a distillation column means the highest temperature liquid media inside the column is exposed to during normal operation. Thus, the operation temperature of a column is typically the temperature of the liquid media in the reboiler, if the column is equipped with a reboiler.

The term "S-containing component" as used herein includes all compounds comprising sulfur.

In the present application, sulfur concentration in a material is expressed in terms of proportion (ppm, weight percentages, and the like) of the weight of elemental sulfur relative to the total weight of the material, even though the sulfur may be present in various valencies other than zero. Sulfuric acid concentration is expressed in terms of proportion (ppm, weight percentages, and the like) of the weight of $H_2SO_4$ relative to the total weight of the material, even though the sulfuric acid may be present in the material in forms other than $H_2SO_4$. Thus, the sulfuric acid concentration is the total concentration of $H_2SO_4$, $SO_3$, $HSO_4^-$, and R—$HSO_4$ in the material.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question, unless otherwise noted. Thus, absent a contrary indication, the concentrations of the various components of a first mixture are expressed based on the total weight of the first mixture. All ranges expressed herein should include both end points as two specific embodiments unless specified or indicated to the contrary.

In the present disclosure, a location "in the vicinity of" an end (top or bottom) of a column means a location within 10% of the top or bottom, respectively, the % being based upon the total height of the column. That is, a location "in the vicinity of the bottom" of a column is within the bottom 10% of the column's height, and a location "in the vicinity of the top" of a column is within the top 10% of the column's height.

An "upper effluent" as used herein may be at the very top or the side of a vessel such as a distillation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent. The "same level" on a distillation column means a continuous segment of the column with a total height no more than 5% of the total height of the column.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6$^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a distillation column.

As used herein, the generic term "dicyclohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, dicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

The process and systems for making cyclohexanone disclosed herein can be advantageously used for making cyclohexanone from any feed mixture comprising phenol, cyclohexanone and cyclohexylbenzene. While the feed may be derived from any process or source, it is preferably obtained from the acid cleavage of a mixture comprising cyclohexylbenzene hydroperoxide and cyclohexylbenzene, which, in turn, is preferably obtained from aerobic oxidation of cyclohexylbenzene, which, in turn, is preferably obtained from benzene hydroalkylation. Steps of these preferred processes are described in detail below.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

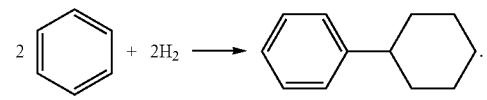

Alternatively, cyclohexylbenzene can be produced by direct alkylation of benzene with cyclohexene in the presence of a solid-acid catalyst such as molecular sieves in the MCM-22 family according to the following Reaction-2:

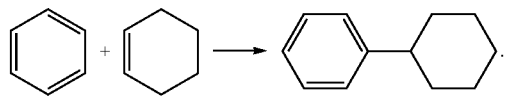

Side reactions may occur in Reaction-1 or Reaction-2 to produce some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step. Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Details of feed materials, catalyst used, reaction conditions, and reaction product properties of benzene hydroalkylation, and transalkylation and dealkylation can be found in, e.g., the following copending, co-assigned patent applications: U.S. Provisional Patent Application Ser. No. 61/972,877, entitled "Process for Making Cyclohexylbenzene and/or Phenol and/or Cyclohexanone;" and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

(Reaction-3)

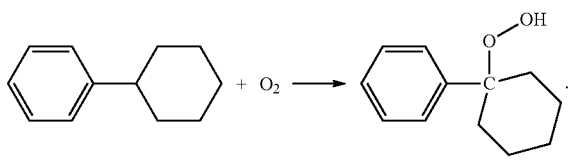

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

In exemplary processes, the oxidation step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor to effect the oxidation.

The oxidation may be conducted in the absence or presence of a catalyst, such as a cyclic imide type catalyst (e.g., N-hydroxyphthalimide).

Details of the feed material, reaction conditions, reactors used, catalyst used, product mixture composition and treatment, and the like, of the oxidation step can be found in, e.g., the following copending, co-assigned patent applications: U.S. Provisional Patent Application Ser. No. 61/972,877, entitled "Process for Making Cyclohexylbenzene and/or Phenol and/or Cyclohexanone;" and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

(Reaction-4)

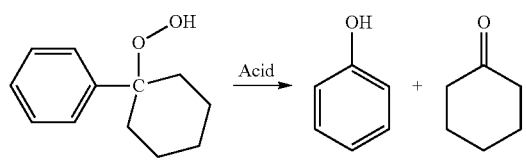

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Feed composition, reaction conditions, catalyst used, product mixture composition and treatment thereof, and the like, of this cleavage step can be found in, e.g., the following copending, co-assigned patent applications: U.S. Provisional Patent Application Ser. No. 61/972,877, entitled "Process for Making Cyclohexylbenzene and/or Phenol and/or Cyclohexanone;" and filed on Mar. 31, 2014; U.S. Provisional Patent Application Ser. No. 62/037,794, entitled "Process and System for Making Cyclohexanone," and filed on Aug. 15, 2014; U.S. Provisional Patent Application Ser. No. 62/037,801, entitled "Process and System for Making Cyclohexanone," and filed on Aug. 15, 2014; U.S. Provisional Patent Application Ser. No. 62/037,814, entitled "Process and System for Making Cyclohexanone," and filed on Aug. 15, 2014; U.S. Provisional Patent Application Ser. No. 62/037,824, entitled "Process and System for Making Cyclohexanone," and filed on Aug. 15, 2014; U.S. Provisional Patent Application Ser. No. 62/057,919, entitled "Process for Making Cyclohexanone," and filed on Sep. 30, 2014; U.S. Provisional Patent Application Ser. No. 62/057,947, entitled "Process for Making Cyclohexanone," and filed on Sep. 30, 2014; and U.S. Provisional Patent Application Ser. No. 62/057,980, entitled "Process for Making Cyclohexanone," and filed on Sep. 30, 2014, the contents of all of which are incorporated herein by reference in their entirety.

Separation and Purification

A portion of the neutralized cleavage reaction product can then be separated by methods such as distillation. In one example, in a first distillation column after the cleavage reactor, a heavies fraction comprising heavies (such as amine sulfuric acid complex, which can be regarded as an amine sulfate salt, if an organic amine is used to neutralize at least a portion of the sulfuric acid present in the cleavage reaction product before it is fed into the first distillation column) is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidation step. Since the cyclohexylbenzene separated from the cleavage product mixture may contain phenol and/or olefins such as cyclohexenylbenzenes, the material may be subjected to treatment with an aqueous composition comprising a base and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower fraction comprising primarily phenol, and some cyclohexanone. Cyclohexanone cannot be completely separated from phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., sulfolane, and glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Where an acid, such as sulfuric acid, is used as the catalyst in the cleavage step, and a liquid amine is used as the neutralizing agent to neutralize at least a portion of the acid before the cleavage product mixture is fed into the first distillation column, the acid will react with the amine to form a complex that is fed into the first distillation column as well. It had been hoped that given the high boiling point of the complex, it would stay in the bottom fraction of the first distillation column, and therefore all sulfur would be removed completely from the bottoms of the first distillation column. However, in a very surprising manner, it has been found that sulfur was present in the fraction comprising cyclohexanone and phenol exiting the first distillation column.

Without intending to be bound by a particular theory, it is believed that the complex between the acid catalyst and the organic amine, if present in the feed to the first distillation column, can decompose at least partially in the first distillation column, due to the high operating temperature therein (i.e., the highest temperature the liquid media is exposed to in the first distillation column, typically in the vicinity of the bottom of the column and/or in the reboiler) of at least 120° C. This temperature is typically necessitated by the separation of cyclohexylbenzene present therein at high concentrations (e.g., ranging from 5 wt % to 50 wt %, based on the total weight of the cleavage product mixture), which has a very high normal boiling temperature (240° C., compared to the normal boiling temperature of cumene of 152° C.). The decomposition of the complex likely produces, among others, $SO_3$, which can easily travel upwards along the first distillation column to upper locations, where it can recombine at least partially with water to form $H_2SO_4$. This operation temperature can be significantly higher than the distillation temperature that the mixture of cumene, phenol, and acetone is exposed to in the first distillation column in the cumene process for making phenol and acetone.

Thus, the presence of acid, especially strong acid such as $SO_3$, $HSO_4^-$, R—$HSO_4$, and/or sulfuric acid in the first distillation column, can catalyze many undesirable side reactions between and among the many components present in the distillation mixture, leading to the formation of byproducts (including S-containing components) and/or premature malfunction of the distillation column. Furthermore, at high operation temperature, prolonged exposure to the acid can cause significant corrosion to the column equipment. The acid species can also make their way into the various fractions drawn from the different locations of the first distillation column, causing different problems in subsequent steps where the fractions are further processed. If the acid species and/or S-containing component enter into a down-stream hydrogenation reactor (described below) where phenol is hydrogenated to make additional cyclohexanone, the hydrogenation catalyst can be easily deactivated.

Therefore, treating the cleavage product mixture before it enters into the first distillation column using a solid-phase basic material according to the present invention is highly advantageous and desirable. Doing so would reduce or eliminate the presence of acid species and/or S-containing components in media inside the first distillation column, avoid undesirable side reactions and byproducts formed as a result of contact with the acid species, reduce corrosion of the first distillation column caused by the acid species and the associated repair and premature replacement, and prevent undesirable side reactions and byproduct formation in subsequent steps.

Such basic materials useful for treatment according to such embodiments, advantageously in solid-phase under the operation conditions, can be selected from (i) oxides of alkali metals (e.g., Na), alkaline earth metals (e.g., Mg), and zinc; (ii) hydroxides of alkali metals (e.g., Na), alkaline earth metals (e.g., Mg), and zinc; (iii) carbonates of alkali metals (e.g., Na), alkaline earth metals (e.g., Mg), and zinc; (iv) bicarbonates of alkali metals (e.g., Na), alkaline earth metals (e.g., Mg), and zinc; (v) complexes of two or more of (i), (ii), (iii), and (iv); (vi) solid amines; (vii) ion-exchange resins; and (viii) mixtures and combinations of two or more of (i), (ii), (iii), (iv), (v), (vi), and (vii). Oxides, hydroxides, carbonates and bicarbonates of alkali and alkaline earth metals and zinc can react with acid to form salts thereof, which preferably, are also in solid-phase under the operation conditions. Preferably, an ion exchange resin is used. Such ion exchange resins preferably comprise groups on the surface thereof capable of adsorbing and/or binding with protons, $SO_3$, $HSO_4^-$, $H_2SO_4$, complexes of sulfuric acid, and the like. The ion exchange resin can comprise a strong and/or a weak base resin. Weak base resins primarily function as acid adsorbers. These resins are capable of sorbing strong acids with a high capacity. Strong base anion resins can comprise quarternized amine-based products capable of sorbing both strong and weak acids. Commercial examples of basic ion exchange resins useful in the present invention include but are not limited to: Amberlyst® A21 and Amberlyst® A26 basic ion exchange resins available from Dow Chemical Company. Amberlyst® A26 is an example of a strong base, type 1, anionic, macroreticular polymeric resin. According to Dow Chemical Company, the resin is based on crosslinked styrene divinylbenzene copolymer, containing quaternary ammonium groups. A26 is generally considered to be a stronger base resin than A21.

After treatment using a solid-phase base and/or ion exchange resin, both total acid concentration and acid precursor concentration (including concentration of S-containing components) in the feed supplied to the first distillation column can be exceedingly low (e.g., 50 ppm or less, such as less than or equal to 20, 15, 10, 5, or 1 ppm). Accordingly, the first distillation column can be operated at a high operation temperature, such as temperatures higher than the disassociation temperatures of complex materials formed between the acid catalyst used in the cleavage step, such as sulfuric acid, and the following organic amines: (i) pentane-1,5-diamine; (ii) 1-methylhexane-1,5-diamine; (iii) hexane-1,6-diamine; (iv) 2-methylpentane-1,5-diamine; (v) ethylene diamine; (vi) propylene diamine; (vii) diethylene triamine; and (viii) triethylene tetramine, without the concern of issues associated with acid produced from thermal dissociation thereof under such high operation temperature.

Separation and Hydrogenation Reaction

At least a portion, preferably the entirety, of the neutralized cleavage effluent (cleavage reaction product), may be separated and a phenol-containing fraction thereof can be provided as a hydrogenation feed which is hydrogenated to convert a portion of the phenol to cyclohexanone in accordance with the present invention. Thus, various embodiments include providing a phenol-containing hydrogenation feed to a hydrogenation reaction zone, wherein the phenol-containing hydrogenation feed comprises the phenol-containing fraction from the aforementioned separation of a cleavage effluent. In some embodiments, the hydrogenation feed may further comprise one or more recycle streams or other streams comprising a higher weight % of either phenol or cyclohexanone, as compared to the phenol-containing stream drawn from separation. Thus, in various embodiments, the hydrogenation feed may have a weight ratio of phenol to cyclohexanone within the range of 0.15-4.0. In certain embodiments the weight ratio is within the range of 0.15 to 0.9 (e.g., where a cyclohexanone-containing stream is combined with the hydrogenation feed, and/or wherein the phenol-containing stream withdrawn from separation of the cleavage reaction product contains most or all of the cyclohexanone in the cleavage reaction product), whereas in others, it is within the range of 1.0 to 4.0, preferably 2.0 to 4.0.

A hydrogenation reaction zone may comprise any one or more hydrogenation reactors, which reactors may be arranged in series, in parallel, or in any combination thereof. For ease of illustration, many figures and their accompanying discussion in the ensuing description include only a single hydrogenation reactor R1, but it should be understood that various embodiments employ multiple hydrogenation reactors arranged in series or in parallel in place of such hydrogenation reactor R1. Further, in embodiments employing multiple hydrogenation reactors (whether in series or in parallel), hydrogen supply may be staged across such multiple reactors, so that each reactor can receive hydrogen feed. A preferred hydrogenation reactor according to some embodiments (any one or more of which may constitute a hydrogenation reaction zone) is a shell-and-tubes type hydrogenation reactor (e.g., as illustrated and discussed below in connection with FIG. 4). Such a reactor may comprise one or more tubes in which hydrogenation catalyst is disposed, and through which hydrogenation reaction feed flows. The tube(s) are themselves disposed within a shell such that the shell carries temperature-control media (e.g., water, refrigerant, or another process stream) capable of absorbing heat from the hydrogenation reaction(s) taking place within the tubes. The fluid flowing through the shell and over the tube(s) may also or instead carry heat to the hydrogenation catalyst disposed within the tubes. For instance, the hydrogenation catalyst may periodically be regenerated by heating (discussed in more detail below), and such heating may be carried out in situ in the hydrogenation reactor by providing heat through a fluid flowing through the shell and over the tube(s).

Figure 5:
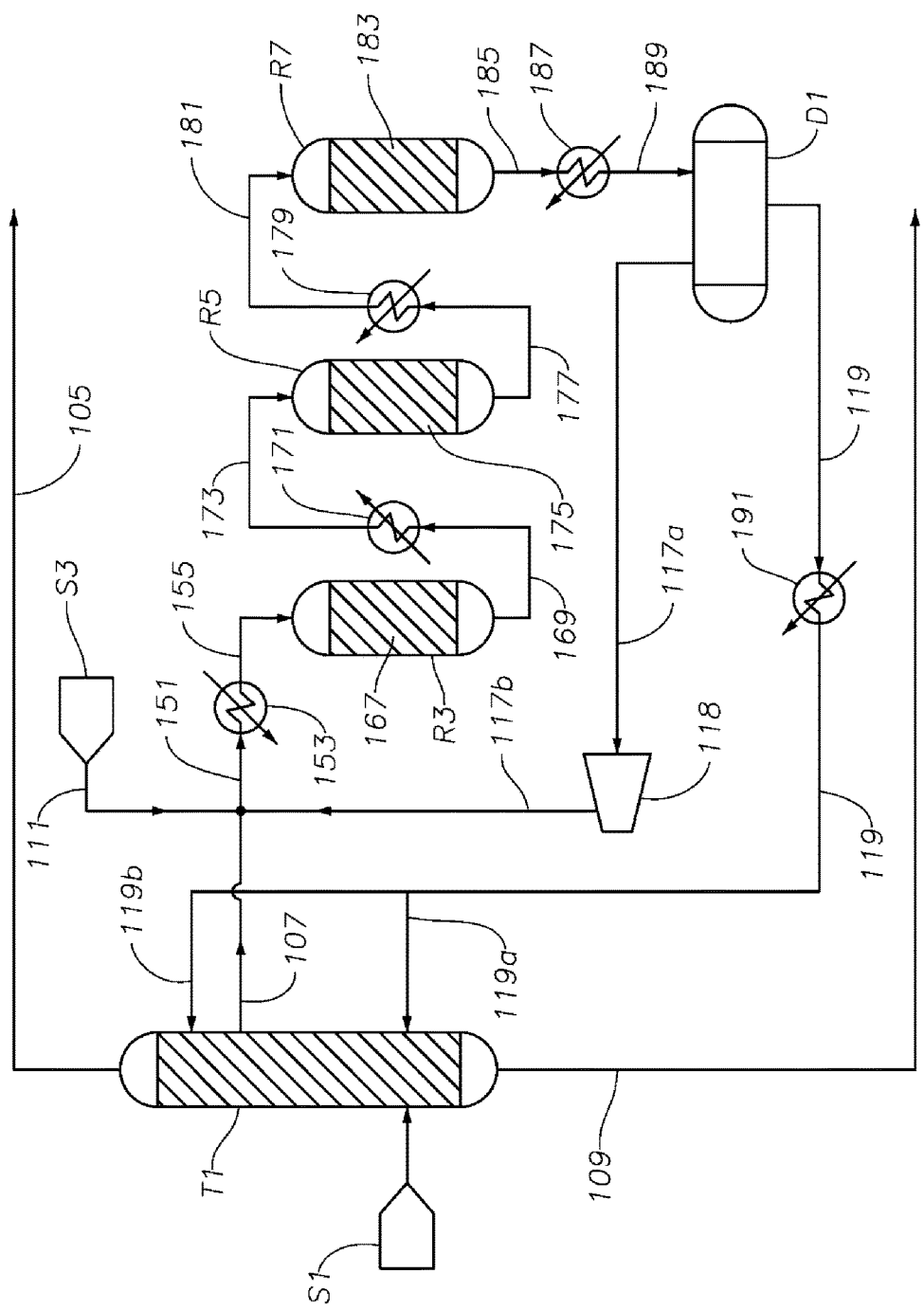
FIG. 5 is a schematic diagram showing a portion of a process/system similar to those shown in FIGS. 1 to 4, but comprising three hydrogenation reactors R3, R5, and R7 connected in series, where the hydrogenation reaction occurs primarily in liquid phase.

The hydrogenation reaction zone (e.g., comprising hydrogenation reactor R1 as shown in FIG. 1, or comprising multiple hydrogenation reactors R3, R5, and R7 as shown in FIG. 5, each described in more detail below) includes a hydrogenation catalyst, in the presence of which various reactions take place. Preferably, each reactor in the hydrogenation reaction zone comprises a bed of hydrogenation catalyst (i.e., a hydrogenation catalyst bed) disposed therein.

The hydrogenation catalyst may comprise a hydrogenation metal performing a hydrogenation function supported on a support material. The hydrogenation metal can be, e.g., Fe, Co, Ni, Ru, Rh, Pd, Ag, Re, Os, Ir, and Pt, and mixtures and combinations of one or more thereof. Pd is a particularly preferred hydrogenation metal according to some embodiments. The concentration of the hydrogenation metal can be, e.g., in a range from 0.001 wt % to 7.5 wt % (such as 0.01 wt % to 5.0 wt %), based on the total weight of the catalyst. Preferably, the metal is present in its fully reduced metal state (e.g., $Pd^0$ as opposed to Pd oxide ($Pd^{+2}$ oxidation state)). The support material can be advantageously an inorganic material, such as oxides, glasses, ceramics, molecular sieves, and the like. For example, the support material can be activated carbon, $Al_2O_3$, $Ga_2O_3$, $SiO_2$, $GeO_2$, SnO, $SnO_2$, $TiO_2$, $ZrO_2$, $Sc_2O_3$, $Y_2O_3$, alkali metal oxides, alkaline earth metal oxides, and mixtures, combinations, complexes, and compounds thereof. Preferred supports include $Al_2O_3$ and/or activated carbon. Hydrogenation catalysts according to certain embodiments may further comprise an alkali or alkaline earth metal dopant (e.g., a sodium dopant) in amounts ranging from about 0.1 to about 3 wt %, such as about 0.5 to 1.5 wt %. Furthermore, without wishing to be bound by theory, it is believed that the preferred hydrogenation reaction occurs quickly in the presence of the hydrogenation metal. Therefore, it is highly desirable that the hydrogenation metal is preferentially distributed in the outer rim of the catalyst particles, i.e., the concentration of the hydrogenation metal in the catalyst particle surface layer is higher than in the core thereof. Such rimmed catalyst can reduce the overall hydrogenation metal loading, reducing cost thereof, especially if the hydrogenation metal comprises a precious metal such as Pt, Pd, Ir, Rh, and the like. The low concentration of hydrogenation metal in the core of the catalyst particle also leads to a lower chance of hydrogenation of cyclohexanone, which may diffuse from the surface to the core of the catalyst particles, resulting in higher selectivity of cyclohexanone in the overall process.

It is believed that the catalyst surface can have different degrees of adsorption affinity to the different components in the reaction media such as phenol, cyclohexanone, cyclohexanol, cyclohexenone, cyclohexylbenzene, and bicyclohexane. It is highly desired that the catalyst surface has higher adsorption affinity to phenol than to cyclohexanone and cyclohexylbenzene. Such higher phenol adsorption affinity will give phenol competitive advantages in the reactions, resulting in higher selectivity to cyclohexanone, lower selectivity of cyclohexanol, and lower conversion of cyclohexylbenzene, which are all desired in a process designed for making cyclohexanone.

Figure 10:
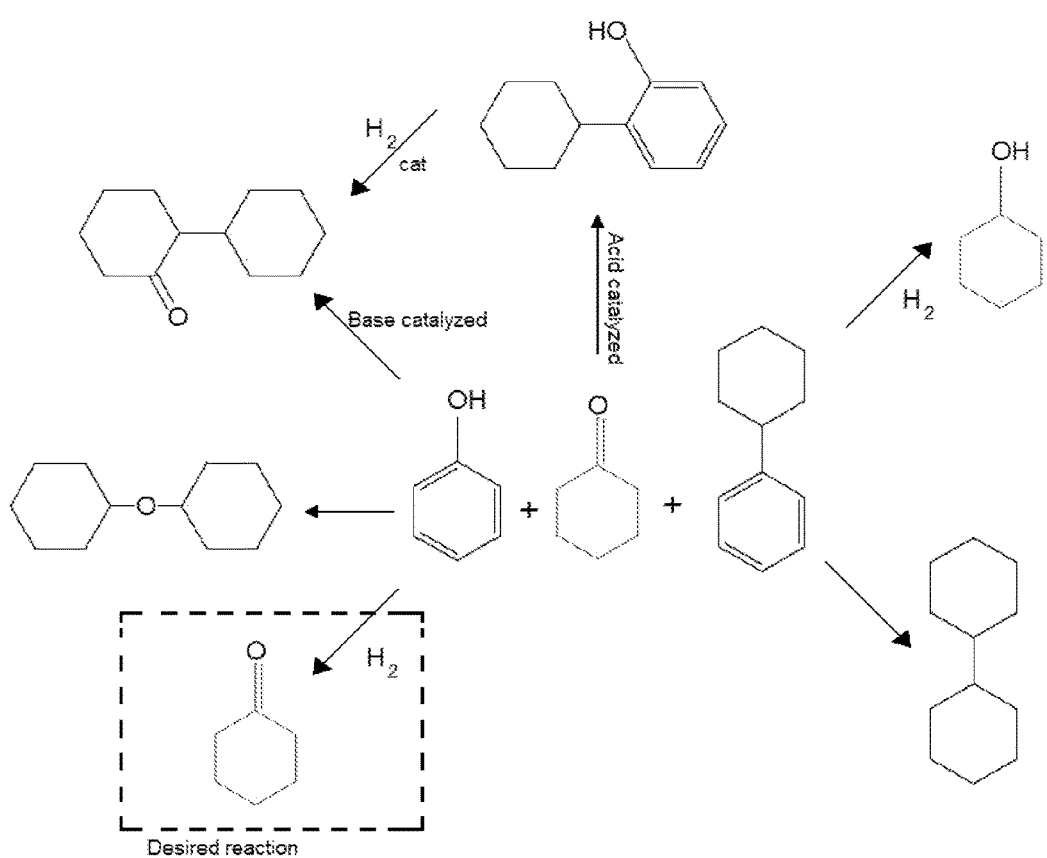
FIG. 10 is a diagram illustrating potential chemical reactions that could take place in a hydrogenation reaction zone to which a hydrogenation feed is provided in accordance with some embodiments.

As noted, numerous reactions may take place in the hydrogenation reaction zone. The possibilities are generally complicated as compared to conventional phenol hydrogenation reactions by virtue of the presence of cyclohexanone and cyclohexylbenzene in the feed. FIG. 10 illustrates various reactions that are possible from these three major components of the hydrogenation feed (phenol, cyclohexanone, and cyclohexylbenzene). FIG. 10 also points out the desired hydrogenation reaction, that of phenol to cyclohexanone:

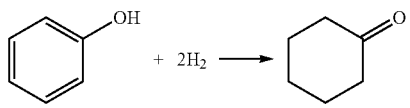 [SMILES: Oc1ccccc1 ; O=C1CCCCC1]

Other reactions may take place, as well, such as the hydrogenation of cyclohexenone (which may be present in the hydrogenation feed in amounts such as 0.01 wt % to 5 wt %, by weight of the feed exclusive of hydrogen) to cyclohexanone:

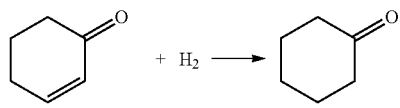 [SMILES: O=C1C=CCCC1 ; "H2" ; O=C1CCCCC1]

Advantageously, however, this side reaction produces the desired cyclohexanone product.

To further complicate matters, various impurities may be present in the hydrogenation feed (e.g., from one or more upstream processes in accordance with the hydroalkylation, oxidation, and cleavage reaction processes described previously). For instance, the hydrogenation feed may further comprise cyclohexanol and/or other oxygenated hydrocarbon compounds produced as byproducts of interactions between components in previously-described upstream processes, such as condensation reaction products.

Furthermore, certain light components, such as organic acids (e.g., formic acid, acetic acid, propanoic acid, linear, linear branched and cyclic carboxylic acids comprising 5, 6, 7, or 8 carbon atoms such as benzoic acid), N-containing compounds (e.g., amines, imides, amides, $NO_{2-}$ substituted organic compounds), and S-containing compounds (e.g., sulfides, sulfites, sulfates, sulfones, $SO_3$, $SO_2$) may be present in the hydrogenation feed. Such light components, if contained in the reaction mixture in the hydrogenation reactor and allowed to contact the hydrogenation metal under the hydrogenation reaction conditions, may poison the hydrogenation catalyst, leading to reduction of performance or premature failure of the catalyst. The aforementioned light components (organic acids, N-containing compounds, and S-containing compounds) are therefore also referred to as catalyst poison components. To avoid catalyst poisoning, it is highly desirable that the hydrogenation feed comprises such catalyst poison components at low concentrations (such as 0 to 5000 wppm each, preferably 0 to 1000 wppm each, such as 1 wppm to 100 wppm).

Pre-Hydrogenation Treatments

In view of the foregoing, certain embodiments include treating one or more of: (1) a hydrogen feed stream and (2) a hydrogenation feed stream comprising phenol, cyclohexanone, and cyclohexylbenzene supplied to a hydrogenation reaction zone, using one or more pre-hydrogenation treatments in order to, e.g., (i) remove impurities; (ii) suppress undesired side reactions; and/or (iii) improve catalyst life and/or selectivity to the desired cyclohexanone product, among other reasons. In general, such feed treatment may be applied to a hydrogen feed stream, and/or to any one or more hydrogenation feed streams, such as any one or more of the hydrogenation feed streams illustrated herein: (i) stream 107 of any one or more of FIGS. 1-8; (ii) stream 107a of FIG. 3; (iii) stream 151 of any one or more of FIGS. 4, 6, and 8; (iv) stream 155 of FIG. 4; and (iv) stream 195 of FIG. 8. In other words, hydrogenation feed treatments discussed herein may be applied to a phenol-containing process stream at any point between (1) initial separation of the cleavage effluent into at least the phenol-containing stream (e.g., in a first distillation column such as distillation column T1 of FIGS. 1-8) and (2) provision of the phenol-containing process stream to a hydrogenation reaction zone (e.g., hydrogenation reactor R1 of FIGS. 1-2 and 4, and/or hydrogenation reactors R3, R5, and R7 of FIG. 5). In some embodiments, such treatments need not be applied to a hydrogenation stream, but also or instead may be applied directly to a hydrogenation reaction zone itself (e.g., a compound provided as a pre-hydrogenation treatment may be supplied via one or more feed streams provided to the hydrogenation reaction zone separately from the hydrogenation feed stream).

Pre-hydrogenation treatment according to some embodiments includes passing a hydrogenation feed stream through one or more sorbents and/or one or more additional distillation columns (referred to herein as "posterior sorbents" and "posterior distillation columns," indicating downstream relationship relative to the separation of cleavage effluent or other stream into at least a phenol-containing stream, e.g., via first distillation column T1 as shown in FIG. 1). See the discussion accompanying FIG. 8 below for additional details regarding posterior sorbents and/or posterior distillation columns according to such embodiments. Such posterior sorbent and/or posterior distillation treatment may be instead of or in addition to the treatment of cleavage reaction product to remove catalyst poison components such as S-containing components prior to separation of the cleavage reaction product, discussed above.

Pre-hydrogenation treatment according to other embodiments may also or instead include the addition of basic chemical agents to the hydrogenation feed stream in order to condition the hydrogenation catalyst (e.g., by tuning the acidity of the catalyst). Suitable basic chemical agents include one or more bases selected from the group consisting of amines, soluble inorganic bases, and mixtures thereof. Such chemical agents are added to the hydrogenation feed as solutions, or are dissolved into the feed (as opposed to passing the feed through solid-phase basic ion exchange resin, per the previous description). Alternatively or in addition, such chemical agents may be provided directly to the hydrogenation reaction zone separately from the hydrogenation feed. Preferred examples of amine chemical agents include alkylamines, such as the primary, secondary, and tertiary alkylamines, cyclic amines, etc., regardless of carbon type or chain length (e.g., methylamine, monoethanolamine, dimethylamine as particular examples). Preferred examples of inorganic base chemical agents include alkali metal and alkaline earth metal compounds (e.g., NaOH and $Na_2CO_3$ in particular). Without wishing to be bound by theory, it is believed that such agents may condition the acidity inherent in hydrogenation catalysts according to some embodiments. For instance, various hydrogenation catalyst supports (e.g., $Al_2O_3$, activated carbon) contain varying degrees of acidic sites; addition of a basic chemical agent to a hydrogenation feed may result in such basic chemical agents reacting with the catalyst's acidic sites, so as to reduce the acidity of the catalyst. This may improve catalyst life and/or phenol conversion rate, and/or cyclohexanone selectivity. Furthermore, addition of such basic chemical agents (e.g., $Na_2CO_3$) may lower the selectivity to cyclohexanol and may inhibit the undesired hydrogenation of cyclohexylbenzene present in the hydrogenation feed. Such chemical agents are preferably supplied to the hydrogenation feed stream and/or hydrogenation reaction zone in amounts ranging from about 0.01 to 5 wt %, preferably 0.01 to 0.1 wt %, most preferably about 0.03 to 0.07 wt %, on the basis of hydrogenation feed (exclusive of hydrogen and any inert fluids that may be provided to the hydrogenation reaction zone with the hydrogenation feed).

Pre-hydrogenation treatment according to yet further embodiments also or instead includes providing water to one or more of a hydrogenation feed stream or the hydrogenation reaction zone. Water may be added in amounts ranging from about 0.1 wt % to 20 wt %, on the basis of hydrogenation feed provided to the hydrogenation reaction zone (exclusive of hydrogen and any inert fluids provided to the hydrogenation reaction zone). In some embodiments, water is added in relatively low amounts (e.g., preferably 0.1 wt % to 3 wt %, such as 1 wt % to 3 wt %), whereas in other embodiments, water is added in relatively high amounts (e.g., preferably 5 wt % to 20 wt %, such as 6 wt % to 15 wt %). In certain embodiments where water is added in relatively high amounts, the amount of water added is based upon the phenol present in the hydrogenation feed. For instance, phenol may be added at a water:phenol weight ratio of at least 0.10, more preferably at least 0.12, such as at least 0.15. Addition of water according to some embodiments may serve multiple useful purposes. For instance, it may suppress various undesired side reactions. In particular, it may suppress the undesired side reaction of hydrogenation of cyclohexylbenzene. It is hypothesized that a small amount of water may form a hydrophilic layer on the hydrogenation catalyst surface, preventing the diffusion of cyclohexylbenzene to the catalyst surface (and thereby inhibiting the catalyzed hydrogenation of cyclohexylbenzene), while permitting the more polar phenol compounds to continue to diffuse to the catalyst, where the phenol is hydrogenated. Water may also suppress the formation of condensation products from components in the hydrogenation feed (e.g., aldols and the like). Since water is formed as a product of such equilibrium-driven reactions, the presence of water may suppress the occurrence of such reactions. This is advantageous insofar as the non-water condensation products may adsorb to the hydrogenation catalyst, plugging sites that could otherwise be used by phenol to be hydrogenated, and thereby significantly decreasing the conversion of phenol over the hydrogenation catalyst as time passes.

It should also be noted that in some embodiments, a chemical agent (e.g., $Na_2CO_3$) may be supplied to the hydrogenation feed stream and/or the hydrogenation reaction zone as an aqueous solution. The aqueous solution may be provided in amounts sufficient to provide the aforementioned amounts of water to the hydrogenation reaction zone, thereby effectively combining two treatment methods.

Pre-hydrogenation treatment according to further embodiments includes diluting a hydrogen feed stream to the hydrogenation reaction zone with an inert fluid, such as nitrogen, methane, steam, or any other substance capable of controlling the hydrogenation reaction selectivity by reducing or diminishing the hydrogen partial pressure in the reaction zone. Such hydrogen partial pressure will vary with reactor operating pressure. A convenient way to represent the hydrogen partial pressure effect on the hydrogenation process is to operate at a desired hydrogen to phenol molar ratio, which may range from about 0.1 to 6.0 (preferably about 2.0 to about 4.0) moles hydrogen to moles phenol fed to the hydrogenation reaction zone.

Yet further embodiments include temporarily introducing one or more hydrogenation catalyst inhibitors to the hydrogenation feed and/or the hydrogenation reaction zone (that is, continuously introducing the catalyst inhibitor for only a limited period of time that is shorter than the period of time during which hydrogenation feed is continuously introduced to the hydrogenation reaction zone). A "catalyst inhibitor" as used herein should be understood as any compound that is capable of temporarily and reversibly suppressing the activity of a hydrogenation catalyst (e.g., by reversibly adsorbing to active hydrogenation metal sites on the catalyst). A catalyst inhibitor is distinct from a catalyst poison component insofar as the catalyst inhibitor's effect may be readily controlled so as to be temporary and reversible during normal process conditions simply by ceasing the supply of the catalyst inhibitor. For instance, the catalyst inhibitor CO may adsorb onto active metal sites on the hydrogenation catalyst, but be readily desorbed by other components of the hydrogenation feed and/or hydrogen feed. Thus, once continuous flow of CO to the hydrogenation reaction zone stops, the remaining CO will desorb, restoring catalyst activity. Such a temporary effect is advantageous during start-up of a process with fresh catalyst (e.g., freshly-reduced, activated catalyst), which may be hyper-active. Such highly active catalyst may promote a higher-than-desired phenol hydrogenation rate, which could lead to excessive, difficult to control, heat release. Excessively high catalyst activity may also cause formation of undesired byproducts (e.g., via hydrogenation of cyclohexanone to cyclohexanol).

Accordingly, processes according to some embodiments include continuously introducing hydrogen, a hydrogenation feed, and a catalyst inhibitor to the hydrogenation reaction zone (e.g., as a separate feed or as part of the hydrogenation and/or hydrogen feed) during a first time period so as to inhibit activity of a hydrogenation catalyst disposed within the hydrogenation reaction zone (e.g., by adsorbing onto one or more active hydrogenation metal sites on the catalyst), and subsequently ceasing the introduction of the catalyst inhibitor to the hydrogenation reaction zone so as to stop the inhibition of hydrogenation catalyst activity (e.g., by allowing the catalyst inhibitor to desorb from the one or more active hydrogenation metal sites on the catalyst), and thereafter continuing to introduce the hydrogen and the hydrogenation feed into the hydrogenation reaction zone during a second time period subsequent to the first time period. Suitable catalyst inhibitors include CO, and, potentially, $H_2S$ at low levels. Preferably, the catalyst inhibitor is CO. Catalyst inhibitor is fed as a vapor, in a range from 0 vol % to 1 vol % on the basis of hydrogen fed to the hydrogenation reaction zone, preferably 1 to 100 vppm (on the basis of hydrogen fed to the hydrogenation reaction zone).

Catalyst Regeneration/Rejuvenation

Notwithstanding the use of the foregoing pre-hydrogenation treatments, hydrogenation catalyst activity may still decrease as normal operation of a hydrogenation reaction zone progresses over time. Accordingly, some embodiments provide for methods for regenerating and/or rejuvenating the hydrogenation catalyst disposed within one or more hydrogenation reactors of a hydrogenation reaction zone.

Methods according to some such embodiments advantageously include on-stream catalyst regeneration or rejuvenation (i.e., regeneration or rejuvenation that takes place while hydrogenation feed is provided to the hydrogenation reaction zone, so as to allow for the desired phenol hydrogenation while the catalyst is being regenerated). A particular example of such a process is mixed-phase operation of the hydrogenation reaction, meaning that the hydrogenation reaction medium (comprising unreacted hydrogenation feed and any products and byproducts formed within the reaction zone) contacting the hydrogenation catalyst within the hydrogenation reaction zone is in mixed liquid and vapor phase. It is believed that when at least a portion of the hydrogenation feed contacting the hydrogenation catalyst is maintained in liquid phase, the liquid phase portion of the feed serves as a liquid wash, which removes impurities (e.g., hydrocarbon and/or oxygenate impurities, catalyst poisons, and the like) that have adsorbed or absorbed onto the hydrogenation catalyst (either on active metal sites or on the support, so as to block phenol's access to active metal sites). The impurities may be removed by physical effects and/or chemical interaction with the partially liquid-phase flow (e.g., the liquid may displace the impurities, and/or the impurities may be at least partially soluble in the liquid-phase reaction medium contacting the catalyst bed, such that the impurities are dissolved within the passing liquid). In order to provide this washing effect, it is preferred that liquid hold-up and/or liquid flux through a bed of hydrogenation catalyst be maintained at or above certain levels. Thus, during mixed-phase operation according to some embodiments, liquid holdup in a hydrogenation reaction zone (e.g., a hydrogenation reactor) should be maintained at greater than or equal to 1 vol %, based upon the available void volume in the hydrogenation catalyst bed within the hydrogenation reaction zone. Preferably, liquid mass flux through the hydrogenation catalyst bed is at least 2 kg/m$^2$s. Where the hydrogenation reaction zone comprises multiple hydrogenation catalyst beds (e.g., where the hydrogenation reaction zone comprises multiple hydrogenation reactors, and/or comprises one or more shell-and-tube hydrogenation reactors with multiple tubes), the liquid mass flux through each catalyst bed is at least 2 kg/m$^2$s. Liquid mass flux is determined based upon the cross-sectional area through which the liquid passes (e.g., the cross-sectional area of the catalyst bed, or, where the catalyst bed is disposed within a hydrogenation reactor, the cross-sectional area of the reactor).

Generally, mixed-phase operation is obtained by adjusting and/or maintaining hydrogenation reaction conditions (particularly temperature and/or pressure). It is well within the ability of an ordinarily skilled artisan to determine suitable combinations of temperature and pressure for mixed-phase operation with minimal experimentation. In particular, an ordinarily skilled artisan will recognize that temperature and pressure are co-dependent (that is, the pressure at which mixed-phase conditions exist depends in part upon the temperature in the hydrogenation reaction zone, and vice-versa). Thus, numerous different combinations of temperature and pressure to arrive at mixed-phase conditions are possible. In general, for a given temperature that is held constant, higher pressure will be needed to move from vapor to mixed-phase. And, for a given pressure that is held constant, lower temperature will be needed to move from vapor to mixed-phase. And, of course, a combination of higher pressure and lower temperature may also be used to move reaction conditions from vapor phase to mixed-phase.

In general, mixed-phase conditions will exist with temperature within the range of 25° C.-250° C., and pressure within the range of 0 kPag to 2000 kPag, while vapor phase operation will include temperature within the range from 100° C. to 300° C. and pressure within the range from 0 kPag to 2000 kPag. For temperatures within the lower end of a given range, pressure may correspondingly be in the lower end of the range. Conversely, when temperature is at the higher end of the range, it will be necessary for pressure to be at the higher end of the range so as to ensure mixed-phase operation. For example, for pressures of 175 kPag or less, temperature in the range of 150 to 200° C. results in vapor-phase operation. But at pressures of around 800 kPag, temperature may range from 100° C. to 200° C. to enable mixed-phase operation. As another example, vapor phase conditions may include about 70 kPag and 165° C.-180° C., while mixed-phase conditions at 70 kPag would exist at 120° C. In some particular embodiments, mixed-phase conditions are maintained by maintaining temperature within the range of 100° C. to 200° C., and maintaining pressure at 800 kPag or less, while adjusting the conditions to simultaneously maintain mixed-phase operation and also maintaining an acceptable hydrogenation reaction rate.

Mixed-phase operation as described above may be maintained as the normal operating condition of the hydrogenation reaction. Thus, methods according to some embodiments include continuously providing hydrogen and hydrogenation feed comprising phenol, cyclohexanone, and cyclohexylbenzene to a hydrogenation reaction zone in which a hydrogenation catalyst bed is disposed, thereby maintaining a reaction medium flowing through the hydrogenation catalyst bed within the hydrogenation reaction zone; and maintaining temperature and pressure in the hydrogenation reaction zone such that the reaction medium flowing through the hydrogenation catalyst bed remains in mixed liquid and vapor phase.

In yet other embodiments, mixed-phase operation may be a temporary departure from standard operating conditions (either vapor or liquid phase operations, preferably a departure from standard vapor-phase operating conditions). In particular embodiments, the hydrogenation reaction is normally operated in vapor phase, with one or more temporary departures to operation in the mixed liquid- and vapor-phase so as to achieve a liquid washing effect. Thus, methods according to some embodiments include (a) during a first period of time, flowing (i) hydrogen and (ii) a vapor-phase hydrogenation feed comprising phenol, cyclohexanone, and cyclohexylbenzene through a hydrogenation catalyst bed so as to hydrogenate at least a portion of the phenol in the vapor-phase hydrogenation feed to cyclohexanone, and further so as to form one or more hydrocarbon and/or oxygenate impurities that adsorb or absorb onto at least a portion of the hydrogenation catalyst bed; and (b) during a second period of time subsequent to the first period of time, flowing (i) hydrogen and (ii) a mixed liquid- and vapor-phase hydrogenation feed comprising phenol, cyclohexanone, and cyclohexylbenzene through the hydrogenation catalyst bed so as to hydrogenate at least a portion of the phenol in the mixed liquid- and vapor-phase hydrogenation feed to cyclohexanone, and further so as to remove at least a portion of the one or more hydrocarbon and/or oxygenate impurities from the hydrogenation catalyst bed.

Methods according to yet further embodiments of temporary mixed-phase operation include: (a) during a first period of time, continuously providing hydrogen and a hydrogenation feed to a hydrogenation reaction zone in which hydrogenation catalyst is disposed, thereby maintaining a reaction medium flowing through the hydrogenation catalyst bed within the hydrogenation reaction zone, while maintaining initial temperature and initial pressure conditions within the hydrogenation reaction zone such that the reaction medium is entirely in vapor phase during the first period of time; (b) adjusting the initial temperature conditions, the initial pressure conditions, or both, within the hydrogenation reaction zone to obtain liquid washing temperature and pressure conditions within the hydrogenation reaction zone, such that the reaction medium is in mixed liquid and vapor phase after the adjusting; and (c) during a second period of time subsequent to the first period of time, maintaining the liquid washing temperature and pressure conditions within the hydrogenation reaction zone while continuously providing the hydrogen and the hydrogenation feed to the hydrogenation reaction zone, thereby maintaining the reaction medium flowing through the hydrogenation catalyst bed in mixed liquid and vapor phase.

In yet other embodiments, hydrogenation catalyst regeneration and/or rejuvenation may also or instead be carried out off-stream (that is, in the absence of the provision of hydrogenation feed to a hydrogenation reactor within the hydrogenation reaction zone). Preferably, in such embodiments, the hydrogenation reaction zone comprises multiple hydrogenation reactors configured such that, while one or more of the reactors are taken off-line (e.g., provision of hydrogenation feed to such reactors is halted), the remainder of the reactors remain in normal operation (e.g., hydrogenation feed and hydrogen continue to be supplied to the remainder of the reactors such that phenol hydrogenation continues to take place in the remainder of the reactors). This configuration may be effected by any suitable means, such as parallel operation of the multiple hydrogenation reactors of such hydrogenation reaction zones, and/or by the use of a manifold to enable a hydrogenation feed to be selectively provided to any one or more of a plurality of hydrogenation reactors within the hydrogenation reaction zone.

Once taken out of service, a hydrogenation reactor can be subjected to a purging fluid that is preferably inert when contacted with the hydrogenation catalyst (e.g., any one or more of nitrogen, methane, steam, or a combination thereof). The purging fluid removes byproducts and other compounds adsorbed, absorbed, or otherwise trapped within the porous structure of the hydrogenation catalyst bed disposed within that reactor. Also or instead, the hydrogenation catalyst may be regenerated by conducting a controlled oxidative burn with dilute air so as to combust hydrocarbons and/or oxygenates trapped within the hydrogenation catalyst as CO, $CO_2$, and $H_2O$. Such dilute air may be generated by mixing air with diluent gases known to those skilled in the art. The catalyst regenerated according to such embodiments is then purged to remove residual oxygen, and is subsequently reduced by flowing a dilute hydrogen stream at process conditions sufficient to attain complete reduction of the catalyst's active hydrogenation metals such as Pd (that is, such metals are converted from their oxide states to their fully reduced metal states). The reactor may then be placed back in service.

Preferably, once a reactor is placed in service in a hydrogenation reaction zone comprising multiple hydrogenation reactors in series, the newly in-service reactor is placed in the tail-end of the multiple series reactors. That is, the hydrogenation reactor subjected to the out-of-service rejuvenation/regeneration procedure just described (i.e., the regenerated reactor) is preferably returned to service by providing the effluent of the most down-stream hydrogenation reactor of the hydrogenation reaction zone to the regenerated reactor.

Separation and Hydrogenation According to Particular Embodiments

Examples of the separation and hydrogenation processes and/or systems according to some particular embodiments are illustrated in the attached drawings and described in detail below. It should be understood that processes and/or systems shown in the schematic, not-to-scale drawings are only for the purpose of illustrating the general material and/or heat flows and general operating principles of particular embodiments in accordance with these illustrations. To simplify illustration and description, some routine components, such as pumps, valves, reboilers, pressure regulators, heat exchangers, recycling loops, condensers, separation drums, sensors, rectifiers, fillers, distributors, stirrers, motors, and the like, are not shown in the drawings or described herein. One having ordinary skill in the art, in light of the teachings herein, can add those components where appropriate.

FIG. 1 is a schematic diagram showing a process/system 101 for making cyclohexanone from a mixture comprising phenol, cyclohexanone and cyclohexylbenzene including a first distillation column T1 (i.e., the first distillation column), a hydrogenation reaction zone comprising a hydrogenation reactor R1, and a cyclohexanone purification column T2 (i.e., the second distillation column). Feed 103 from storage S1, comprising phenol, cyclohexanone, and cyclohexylbenzene, is fed into the first distillation column T1.

Feed 103 can be produced by any method. A preferred method is by cleaving a cyclohexylbenzene hydroperoxide in the presence of an acid catalyst such as sulfuric acid and cyclohexylbenzene as described above. Feed 103 may further comprise impurities other than cyclohexylbenzene such as: hydrogenation catalyst poisons; light components (defined above) such as water, methylcyclopentanone, pentanal, hexanal, benzoic acid, and the like, and heavy components such as methylcyclopentylbenzene, bicyclohexane, sulfate of an organic amine (such as 1,6-hexamethylenediame, 2-methyl-1,5-pentamethylenediamine, ethylenediamine, propylenediamine, diethylenetriamine, and the like) produced by injecting the amine into the cleavage mixture to neutralize the liquid acid catalyst used. Feed 103 may further comprise olefins heavier than cyclohexanone such as phenylcyclohexene isomers, hydroxylcyclohexanone, cyclohexenone, and the like. The cyclohexylbenzene hydroperoxide may be produced by aerobic oxidation of cyclohexylbenzene in the presence of a catalyst such as NHPI as described above. The cyclohexylbenzene may be produced by hydroalkylation of benzene in the presence of a hydrogenation/alkylation bi-functional catalyst as described above.

Thus, feed 103 (the first mixture) may comprise, based on the total weight thereof:

10 wt % to 90 wt % (such as about 20 wt % to about 30 wt %, or 20 wt % to about 40 wt %) cyclohexanone;

10 wt % to 90 wt % (such as about 20 wt % to about 30 wt %, or 20 wt % to about 40 wt %) phenol (further, the ratio of wt % cyclohexanone to wt % phenol in the feed is preferably from 0.5 to 1.5);

0.001 wt % to 90 wt % (preferably 20 wt % to 70 wt %, such as 30 wt % to 60 wt %) cyclohexylbenzene;

0.001 wt % to 1 wt % bicyclohexane; and light components (e.g., water, benzoic acid, and other carboxylic acids comprising 1 to 8 carbon atoms), S-containing compounds, and N-containing compounds each at a concentration ranging from about 0.1 ppm to 10,000 ppm, preferably 1 to 5000 ppm.

From the first distillation column T1, a first upper effluent 105 comprising a portion of the cyclohexanone and a portion of light components such as water, methylcyclopentanone, and the like, is produced in the vicinity of the top of the column T1. Effluent 105 may comprise, based on the total weight thereof:

60 wt % to 99.9 wt %, preferably 75 wt % to 95 wt % or 99.9 wt %, cyclohexanone;

0 wt % to 1 wt % of each of phenol, cyclohexylbenzene, and bicyclohexane;

0.001 wt % to 10 wt % (preferably 0.1 to 5.0 wt %) cyclohexanol; and light components at a total concentration of 0.001 wt % to 5.0 wt % (preferably 0.001 wt % to 1.0 wt %).

The first upper effluent 105 is then sent to a cyclohexanone purification column T2, from which a third upper effluent 121 comprising light components such as water, methylcyclopentanone, and the like, is produced at a location in the vicinity of the top of column T2 and then delivered to storage S5. A second upper effluent 123 comprising essentially pure cyclohexanone is produced and sent to storage S7. In the vicinity of the bottom of column T2, a second lower effluent 125 is produced and delivered to storage S9. The second lower effluent can be, e.g., a KA oil comprising both cyclohexanone and cyclohexanol. Thus, the second upper effluent 123 may comprise, based on the total weight thereof, 95 to 99.9999 wt % (such as 95 wt % to 99.9 wt %) cyclohexanone. The second lower effluent 125 may comprise, based on the total weight thereof: 10 wt % to 80 wt % cyclohexanol; and 10 wt % to 80 wt % (such as 10 wt % to 40 wt %) cyclohexanone.

The first middle effluent 107 produced from the first distillation column T1 is a phenol-containing stream comprising phenol at a concentration higher than in feed 103 and higher than in the first upper effluent 105, cyclohexanone at a concentration lower than in both feed 103 and the first upper effluent 105, cyclohexylbenzene at a concentration desirably lower than in feed 103 and higher than in the first upper effluent 105, and further comprising one or more of other impurities such as bicyclohexane and cyclohexenone. Thus, effluent 107 may comprise, based on total weight thereof:

1 wt % to 50 wt % (such as 5 wt % to 30 wt %) cyclohexanone;

10 wt % to 80 wt % (such as 20 wt % to 80 wt %) phenol, further wherein the weight ratio of phenol to cyclohexanone is preferably within the range from 1.0 to 4.0, more preferably from 2.0 to 4.0;

0.001 wt % to 30 wt % (such as 0.001 wt % to 10 wt %) cyclohexylbenzene;

0.001 wt % to 30 wt % (such as 0.001 wt % to 25 wt %) bicyclohexane;

0.01 wt % to 30 wt % (such as 0.01 wt % to 5 wt %) cyclohexanol; and light components (e.g., water, benzoic acid, and other organic acid comprising 1, 2, 3, 4, 5, 6, 7, or 8 carbon atoms), S-containing compounds, and N-containing compounds each at a concentration of 0 wppm to 5000 wppm, preferably 0 wppm to 1000 wppm, such as 1 ppm to 1000 ppm.

Effluent 107, if containing catalyst poison components at acceptably low concentration(s), can be directly delivered to a hydrogenation reactor R1, where the effluent 107 is mixed with a hydrogen gas feed 112 comprising fresh make-up hydrogen stream 111 from storage S3 and recycle hydrogen 117. Alternatively, effluent 107 may be subjected to any one or more of the previously described pre-hydrogenation treatments (not shown in FIG. 1). Furthermore, it is contemplated that a hydrogen feed (e.g., hydrogen gas feed 112 or an additional hydrogen feed) may be combined with effluent 107 upstream or downstream of any pre-hydrogenation treatment(s) so as to provide a combined stream of hydrogenation feed and hydrogen to the hydrogenation reaction zone (also not shown in FIG. 1). However provided, the phenol contained in feed 107 and hydrogen reacts with each other in the presence of a hydrogenation catalyst bed 113 inside reactor R1 to produce cyclohexanone. Some of the cyclohexanone inside the reactor R1 reacts with hydrogen in the presence of the catalyst bed 113 as well to produce cyclohexanol. In the exemplary process shown in FIG. 1, surplus hydrogen is fed into reactor R1. It is contemplated that a second phenol-containing stream (not shown), separate from and independent of effluent 107, may be fed into the hydrogenation reactor R1. Such additional feed can advantageously contain 50 wt % to 100 wt % phenol. Preferably, the second phenol-containing stream comprises substantially pure phenol produced by any process, such as the conventional cumene process, coal-based processes, and the like.

The total hydrogenation feed, including stream 107 and optional additional streams (but excluding hydrogen), delivered to the hydrogenation reactor R1, if blended together before being fed into R1, preferably has an overall composition comprising, based on the total weight of the hydrogen feed stream 107 and optional additional streams (excluding hydrogen and any inert fluid provided to the hydrogenation reactor R1):

0.1 to 50 wt % cyclohexanone (such as 0.1 to 50 wt %, more particularly 10 wt % to 50 wt %, even more particularly 20 wt % to 45 wt %);

10 to 99 wt % phenol (such as 30 to 95, or 40 to 85 wt %);

0.001 to 30 wt % of each of cyclohexylbenzene and bicyclohexane (such as 0.1 wt % to 25 wt %, preferably 1 wt % to 20 wt % each); and optionally, depending upon the pre-hydrogenation treatment(s) applied to effluent 107 (if any), any one or more of: (i) 0.1 to 20 wt % water; (ii) 0.01 to 5 wt % of a chemical agent selected from the group consisting of amines, alkali metal compounds, alkaline earth metal compounds, and any combination thereof. In addition, during start-up of the process, one or more catalyst inhibitors may be present in the effluent 107 provided as hydrogenation feed to the hydrogenation reactor R1.

The total amount of hydrogen, including fresh, make-up hydrogen and recycled hydrogen, fed into the reactor R1, and the total amount of phenol fed into the hydrogenation reaction zone desirably exhibit a hydrogen to phenol molar ratio falling within the range of 1:1 to 10:1, preferably within the range of 1:1 to 5:1. While a higher hydrogen-to-phenol ratio can result in higher overall conversion of phenol, it tends to result in higher conversion of cyclohexanone, higher selectivity of phenol to cyclohexanol, and higher conversion of cyclohexylbenzene, as well, making these undesirable side reactions more difficult to control.

At the bottom of reactor R1, a hydrogenation reaction product stream 115 comprising phenol at a concentration lower than in stream 107, cyclohexanone at a concentration higher than in stream 107, cyclohexylbenzene, bicyclohexane, and surplus hydrogen is taken. Stream 115 may comprise, based on the total weight thereof:

20 wt % to 90 wt % (such as 30 wt % or 50 wt % to 90 wt %) Cyclohexanone;

1 wt % to 50 wt % (such as 1 wt % to 15 or 20 wt %) Phenol;

0.001 wt % to 30 wt % (such as 0.001 wt % to 15 wt % or 20 wt %) cyclohexylbenzene;

0.001 wt % to 30 wt % (such as 0.001 wt % to 10 wt % or 15 wt %) bicyclohexane; and 0.01 wt % to 10 wt % (such as 0.01 wt % to 5 wt %) cyclohexanol.

Stream 115 is then delivered to a separation drum D1, where a vapor phase comprising a majority of the surplus hydrogen and a liquid phase is obtained. The vapor phase can be recycled as stream 117 to reactor R1 as part of the hydrogen supply, and the liquid phase 119 is recycled to the first distillation column T1 at one or more side locations on column T1, at least one of which is above the location where the first middle effluent 107 is taken, but below the location where the first upper effluent 105 is taken.

The first bottom effluent 109 obtained from the first distillation column T1 comprises primarily heavy components such as cyclohexylbenzene, bicyclohexane, amine salts (if any), C18+, C12 oxygenates, and C18+ oxygenates. This fraction is delivered to a heavies distillation column T3 (the third distillation column), from which a fourth upper effluent 127 desirably comprising cyclohexylbenzene at a concentration higher than C31 80% and a lower effluent 129 are produced. Effluent 127 may be delivered to storage S11 and effluent 129 to storage S13. Effluent 127 may further comprise olefins, primarily phenylcyclohexene isomers, at a non-negligible amount. It may be desirable to subject effluent 127 to hydrogenation to reduce olefin concentrations, and subsequently recycle the hydrogenated effluent 127 to an earlier step such as cyclohexylbenzene oxidation to convert at least a portion of it to cyclohexylbenzene hydroperoxide, such that the overall yield of the process is improved.

Figure 2:
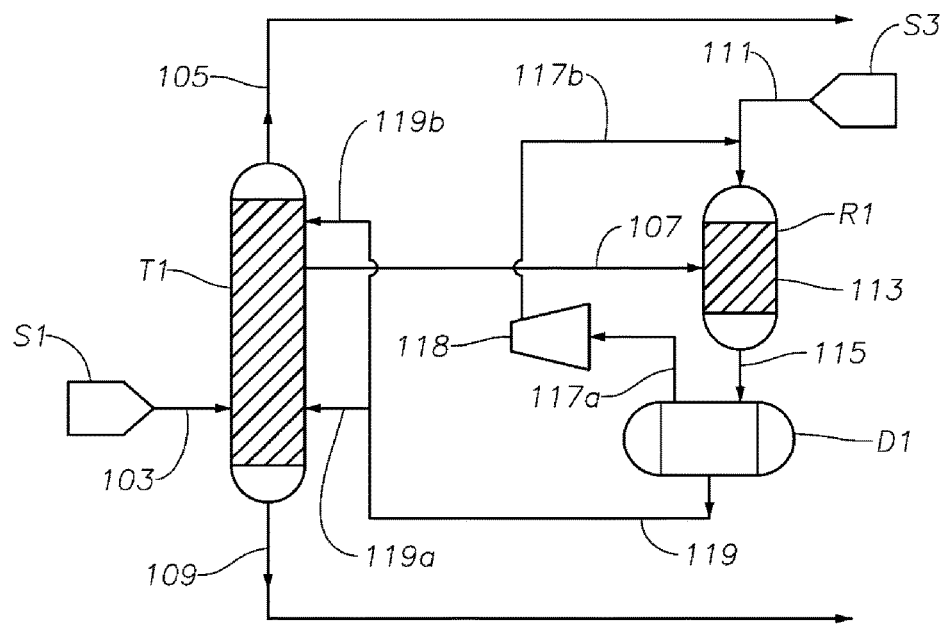
FIG. 2 is a schematic diagram showing a portion of a process/system similar to the process/system shown in FIG. 1, but comprising modified fluid communications between and/or within the first distillation column T1 and the hydrogenation reactor R1.

FIG. 2 is a schematic diagram showing a portion of a process/system similar to the process/system shown in FIG. 1, but comprising modified fluid communications between and/or within the first distillation column T1 and the hydrogenation reactor R1. In this figure, the hydrogenation reaction product 115 comprises residual hydrogen, as in the example shown in FIG. 1. Effluent 115 is first delivered into separation drum D1, where a hydrogen-rich vapor stream 117a is obtained, compressed by a compressor 118, and then delivered to reactor R1 as a stream 117b together with fresh, make-up hydrogen stream 111 into reactor R1. A liquid stream 119 is obtained from separation drum D1, then divided into multiple streams (two recycle streams 119a and 119b shown in FIG. 2), recycled to two different locations on the side of column T1, one below the location where the first middle effluent 107 is taken (shown at approximately the same level as feed 103), and the other above the location where the first middle effluent 107 is drawn. This modified recycle fluid communication between the hydrogenation reactor R1 and the first distillation column T1 compared to FIG. 1 has surprising advantages. It was found that where the recycle liquid stream 119 is fed to one location only, such as at a location above the first middle effluent 107, bicyclohexane is continuously produced in reactor R1 from the cyclohexylbenzene in stream 107, and then steadily accumulates in column T1 to such high concentration that a separate phase can form, interfering with effective product separation in column T1. On the other hand, where the recycle stream 119 is recycled back to column T1 at multiple locations on T1 (as shown in FIG. 2), the probability of forming a separate bicyclohexane phase inside T1 is drastically reduced or eliminated. Such a configuration, then, may substantially reduce the presence of impurities such as bicyclohexane in the final cyclohexanone product.

Figure 3:
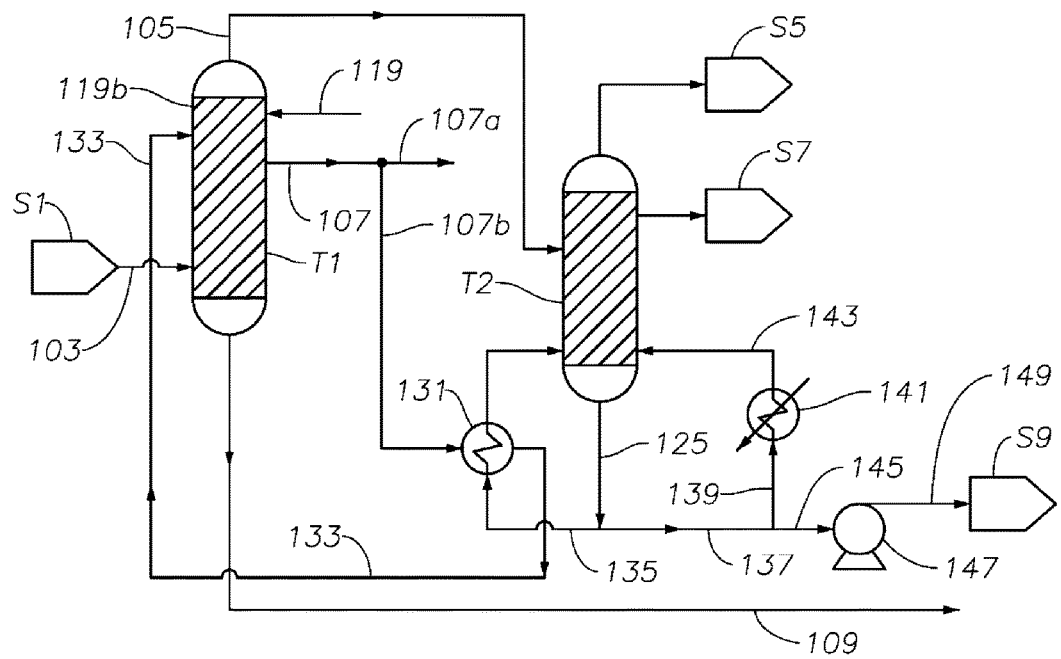
FIG. 3 is a schematic diagram showing a portion of a process/system similar to those shown in FIGS. 1 and 2, but comprising modified fluid communications and/or heat transfer arrangement between and/or within the first distillation column T1 and the cyclohexanone purification column T2.

FIG. 3 is a schematic diagram showing a portion of a process/system similar to those shown in FIGS. 1 and 2 comprising modified fluid communications and/or heat transfer arrangement between and/or within the first distillation column T1 and the cyclohexanone purification column T2. In this figure, the hydrogenation reactor R1 and its peripheral equipment are not shown. In this figure, the first middle effluent 107 drawn from column T1 is divided into multiple streams (two streams 107a and 107b shown), one of which (107a) is delivered to the hydrogenation reactor R1 (not shown) as hydrogenation feed, and the other (107b) to a heat exchanger 131 in fluid and thermal communication with the cyclohexanone purification column T2. In processes according to such embodiments, one or more pre-hydrogenation treatments (not shown) are preferably applied to the stream 107a provided as hydrogenation feed, but the pre-hydrogenation treatment(s) may also or instead be applied to the combined stream 107 prior to division. In this figure, the bottom stream 125 (e.g., comprising a mixture of cyclohexanone and cyclohexanol) from column T2 is divided into three streams: stream 135 which passes through heat exchanger 131 and is heated by stream 107b; stream 139 which is heated by a heat exchanger 141 and then recycled to column T2; and stream 145, which is delivered to storage S9 via pump 147. Stream 107b becomes a cooler stream 133 after passing through heat exchanger 131, and is then subsequently recycled to first distillation column T1 at one or more locations, at least one of which is located above the location where the first middle effluent 107 is drawn. A heat management scheme as illustrated in FIG. 3 can significantly improve the energy efficiency of the overall process and system.

Figure 4:
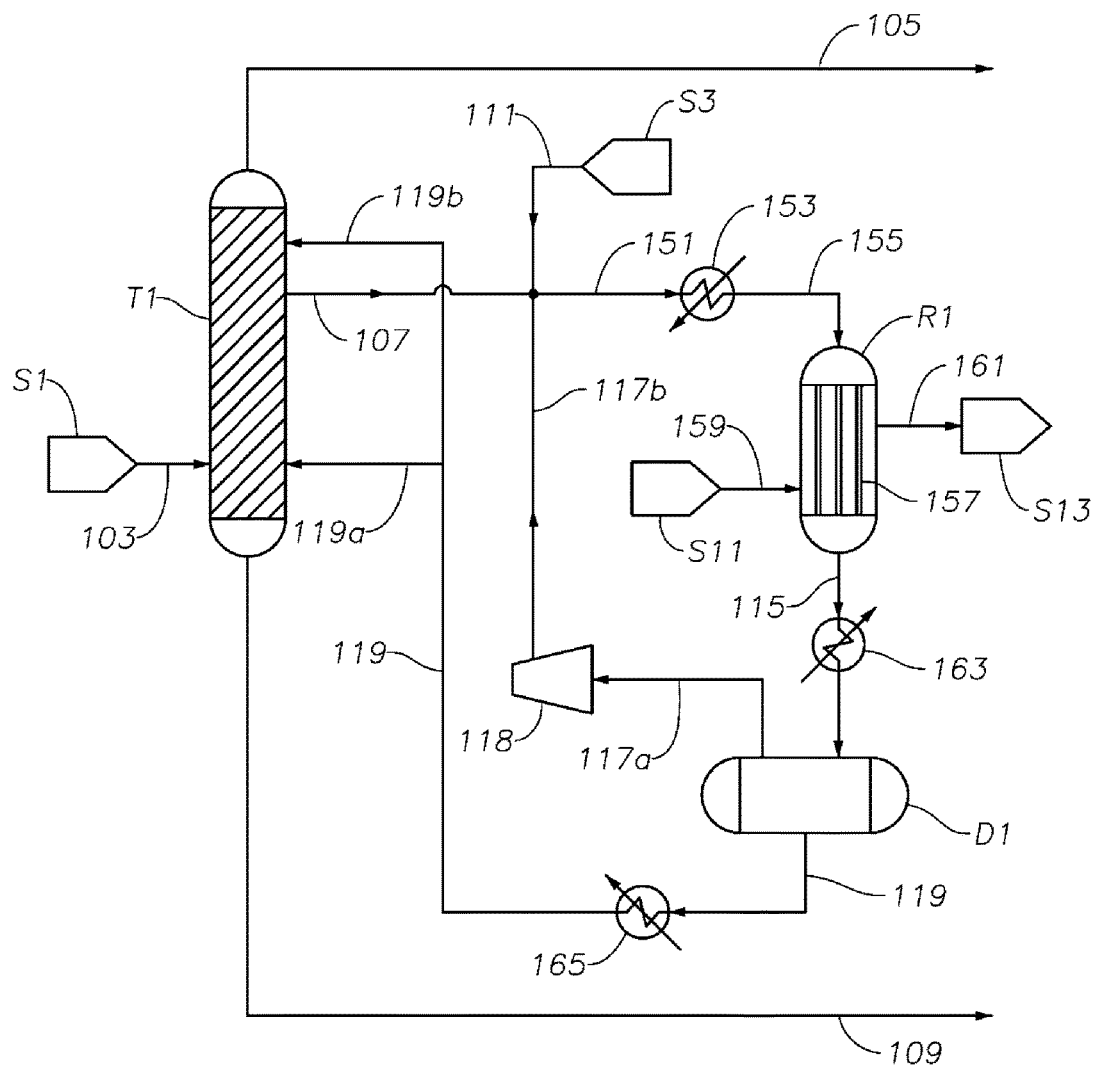
FIG. 4 is a schematic diagram showing a portion of a process/system similar to those shown in FIGS. 1 to 3, but comprising a tubular heat exchanger-type hydrogenation reactor R1, where the hydrogenation reaction occurs primarily in vapor phase.

FIG. 4 is a schematic diagram showing a portion of a process/system similar to those shown in FIGS. 1-3, but comprising a tubular heat exchanger-type hydrogenation reactor R1. This figure illustrates an example where the hydrogenation reactor R1 operates under hydrogenation conditions such that the hydrogenation feed from stream 155 contacts the hydrogenation catalyst in the vapor phase, or in mixed phase, as described previously. In this figure, the first middle effluent 107 taken from the first distillation column T1 is first combined with hydrogen feeds (including fresh make-up hydrogen stream 111 and recycle hydrogen stream 117b), heated by a heat exchanger 153 and then delivered to a tubular heat-exchanger type hydrogenation reaction R1 having hydrogenation catalyst installed inside the tubes 157. It should be noted that in other similar embodiments, the effluent 107 may be provided to the hydrogenation reactor R1 without first being combined with hydrogen feed(s), such that the hydrogen feed(s) are provided directly to the reactor R1. Further, similar to what has been noted in connection with embodiments of FIGS. 1-3, one or more pre-hydrogenation treatments (not shown) may be applied to the effluent 107, or to the combined feed 151 upstream of heat exchange, and/or to the combined feed 153 downstream of heat exchange. In addition, a stream of cooling media 159 such as cold water supplied from storage S11 passes through the shell of the exchanger/reactor R1 and exits the reactor R1 as a warm stream 161 and is then delivered to storage S13, thereby a significant amount of heat released from phenol hydrogenation reaction is carried away, maintaining the temperature inside the reactor R1 in a range from 140° C. to 300° C. (preferably about 220° C. to about 260° C., such as about 240° C.), and an absolute pressure inside the reactor R1 in a range from 100 kPa to 400 kPa (preferably about 180 kPa to about 220 kPa, such as about 200 kPa). Alternatively, the cooling medium may comprise at least a portion of the hydrogenation feed in liquid phase, such that at least a portion of the feed is vaporized, and at least a portion of the vapor feed is then fed to the hydrogenation reactor R1. Further, embodiments operated in accordance with FIG. 4 may include temporary mixed-phase operation (e.g., adjusting the temperature and/or pressure, and maintaining lower temperatures and/or higher pressures for a period of time so as to ensure mixed liquid- and vapor-phase inside the tubes 157). This may be accomplished, e.g., by altering the temperature or flow rate of the cooling medium, or by pressurizing the reactor, or a combination of both. Such operation advantageously provides a liquid washing effect for the hydrogenation catalyst disposed within the tubes 157, as discussed previously.

Because heat transfer of a vapor phase is not as efficient as a liquid phase, and the phenol hydrogenation reaction is highly exothermic, it is highly desired that heat transfer is carefully managed in such vapor phase hydrogenation reactor. Other types of reactors suitable for a liquid phase reaction can be used as well. For example, fixed-bed reactors configured to have intercooling capability and/or quenching options, so that the heat generated in the reaction can be taken away sufficiently quickly to maintain the reaction media in a desirable temperature range.

FIG. 5 is a schematic diagram showing a portion of a process/system similar to those shown in FIGS. 1-4, but with a hydrogenation reaction zone comprising three fixed bed hydrogenation reactors R3, R5, and R7 connected in series. This figure illustrates an example where the hydrogenation reactors operate under hydrogenation conditions such that a majority of the phenol and/or cyclohexylbenzene present in the reaction media inside the reactors R3, R5, and R7 are in liquid phase, although such an arrangement could readily be used for vapor phase reaction, as well (preferably with shell-and-tubes heat exchange reactors as portrayed in FIG. 4). In this figure, the first middle effluent 107 taken from the first distillation column T1 is first combined with hydrogen feeds (including fresh make-up hydrogen stream 111 and recycle hydrogen stream 117b) to form a feed stream 151, then heated by a heat exchanger 153, and then delivered as stream 155 to a first hydrogenation reactor R3 having a catalyst bed 167 inside. Any one or more of streams 107, 151, 153, and 155 may optionally be subjected to one or more pre-hydrogenation treatments. A portion of the phenol is converted to cyclohexanone in reactor R3, releasing a moderate amount of heat raising the temperature of the reaction media. Effluent 169 exiting reactor R3 is then cooled down by heat exchanger 171, and then delivered into a second fixed bed reactor R5 having a catalyst bed 175 inside. A portion of the phenol contained in the reaction media is converted to cyclohexanone in reactor R5, releasing a moderate amount of heat raising the temperature inside the reactor R5. Effluent 177 exiting reactor R5 is then cooled down by heat exchanger 179, and then delivered to a third fixed bed hydrogenation reactor R7 having a catalyst bed 183 inside. A portion of the phenol contained in the reaction media is converted to cyclohexanone in reactor R7, releasing a moderate amount of heat raising the temperature inside the reactor R7. Effluent 185 exiting reactor R7 is then cooled down by heat exchanger 187, and delivered to drum D1, where a vapor phase 117a and a liquid phase 119 are obtained. By using multiple reactors in the hydrogenation reaction zone, and the use of heat exchangers between adjacent reactors and after each reactor, temperatures inside the reactors R3, R5, and R7 are each independently maintained in a range from 140° C. to 300° C. (preferably about 220° C. to about 260° C., such as about 240° C.), and the absolute pressures inside reactors R3, R5, and R7 are each independently maintained in a range from 375 kPa to 1200 kPa (preferably about 1000 to about 1200 kPa, such as about 1134 kPa). In general, higher temperature favors the production of cyclohexanol over cyclohexanone. Thus, it is highly desirable that the hydrogenation is conducted at a temperature no higher than 220° C.

Figure 6:
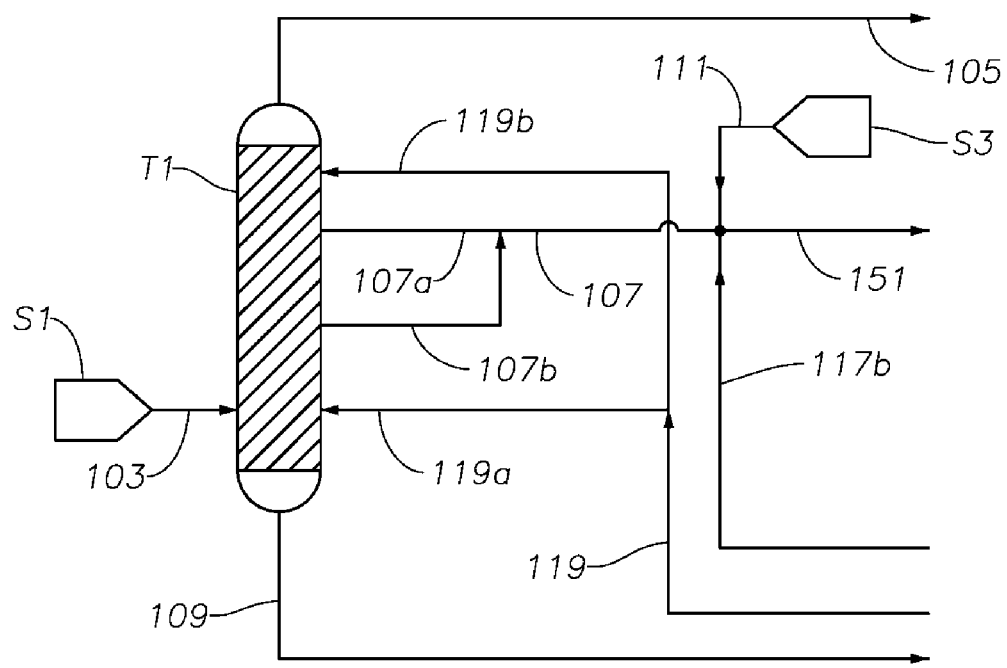
FIG. 6 is a schematic diagram showing a portion of a process/system similar to those shown in FIGS. 1 to 5, but comprising modified fluid communications between and/or within the first distillation column T1 and the hydrogenation reactor R1.

FIG. 6 is a schematic diagram showing a portion of a process/system similar to the process/system shown in FIGS. 1-5, but comprising modified fluid communications between and/or within the first distillation column T1 and the hydrogenation reactor R1. In this figure, two middle effluents, including a first middle effluent 107a and a second middle effluent 107b, are drawn from the side of the first distillation column T1. The two effluents 107a and 107b have differing compositions, and are combined to form a feed 107, which is then combined with hydrogen feed streams 111 and 117b and delivered to the hydrogenation reactor(s) as hydrogenation feed 151 (with any one or more of feed 107 and feed 151 optionally being subjected to one or more pre-hydrogenation treatment(s). Drawing two middle effluents with different compositions at different locations have unexpected technical advantages. It was found that if only one middle effluent is drawn from a single location on column T1, certain undesirable components, such as hydroxycyclohexanone(s), can accumulate in column T1. It is believed that hydroxycyclohexanone(s) can undergo dehydration to form cyclohexenone, which can cause fouling inside column T1. By drawing middle effluents at different height locations on the column, one can effectively reduce the accumulation of such undesirable components and the probability of fouling inside the column.

Figure 7:
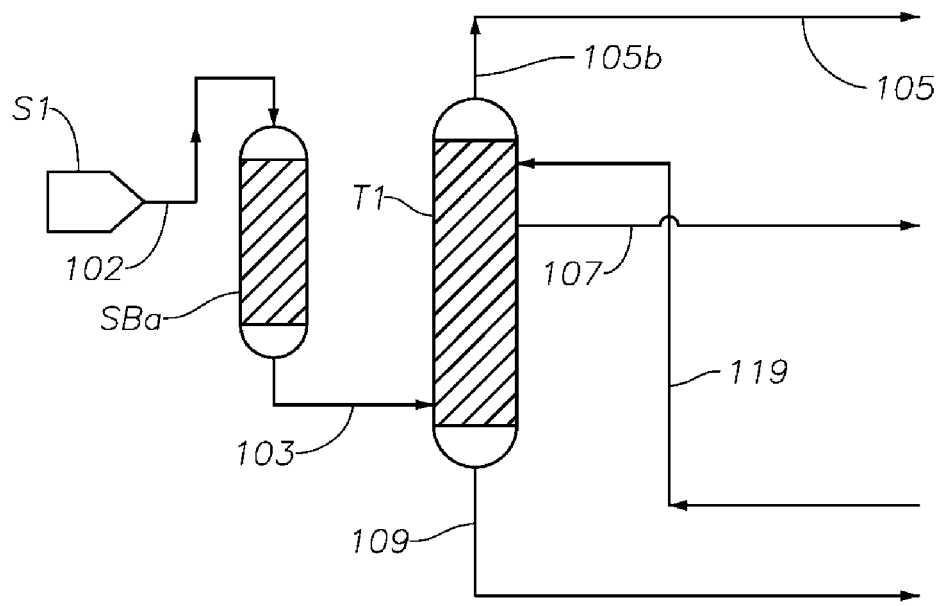
FIG. 7 is a schematic diagram showing a portion of a process/system similar to those shown in FIGS. 1 to 6, but comprising an anterior sorbent bed SBa before the first distillation column T1 configured for removing at least a portion of catalyst poison components from the phenol/cyclohexanone/cyclohexylbenzene feed fed to the first distillation column T1 to reduce or prevent catalyst poisoning in the hydrogenation reactor.

FIG. 7 is a schematic diagram showing a portion of an exemplary process/system of the present disclosure similar to those shown in FIGS. 1-6, but comprising an anterior sorbent bed SBa before the first distillation column T1 configured for removing at least a portion of the S-containing components and/or the light components (especially catalyst poison components) from a crude feed (crude mixture) to reduce or prevent catalyst poisoning in the hydrogenation reactor. A preferred anterior sorbent bed SBa according to some embodiments comprises an Amberlyst® A21 sorbent bed, although other sorbent beds (e.g., a stronger basic ion exchange resin such as Amberlyst® A26) could be used in addition or instead. A crude mixture feed stream 102 is first passed through the sorbent bed SBa, in which a basic solid-phase sorbent material described above is installed. Alternatively, where the total concentration of catalyst poison components (e.g., the S-containing components and other light components capable of poisoning the hydrogenation catalyst) in the crude mixture stream 102 is exceedingly high, an anterior distillation column (not shown) may be used before the anterior sorbent bed SBa, so as to remove a portion of the catalyst poison components from the first mixture fed into the first distillation column Instead or in addition, one or more additional anterior sorbent beds (also not shown in FIG. 7) may be utilized, any one or more of which may be the same or different from the anterior sorbent bed SBa. For instance, a suitable additional anterior sorbent bed could comprise a nickel sorbent, an ion exchange resin, and/or an activated carbon bed. Such sorbents may remove one or more S-containing components, and/or other catalyst poison components, and/or color bodies (i.e., impurities that impart some coloration to the feed stream 102). Desirably, upon treatment by the anterior sorbent bed SBa (and/or the optional anterior distillation column, and/or any one or more additional anterior sorbent beds), concentrations of catalyst poison components capable of poisoning the hydrogenation catalyst is reduced significantly in effluent 107 compared to in feed 102. Thus, in the embodiment shown in FIG. 7, the ratio of concentration of catalyst poison components in the effluent 107 to the concentration of said components in the feed 102 is within the range of about 0.001 to 0.5, preferably about 0.001 to about 0.1, such as 0.001 to 0.1. For instance, the ratio of concentration of sulfuric acid in feed 102 to concentration of sulfuric acid in effluent 107 is preferably within the range of about 0.001 to about 0.1, such as 0.001 to 0.1.

Figure 8:
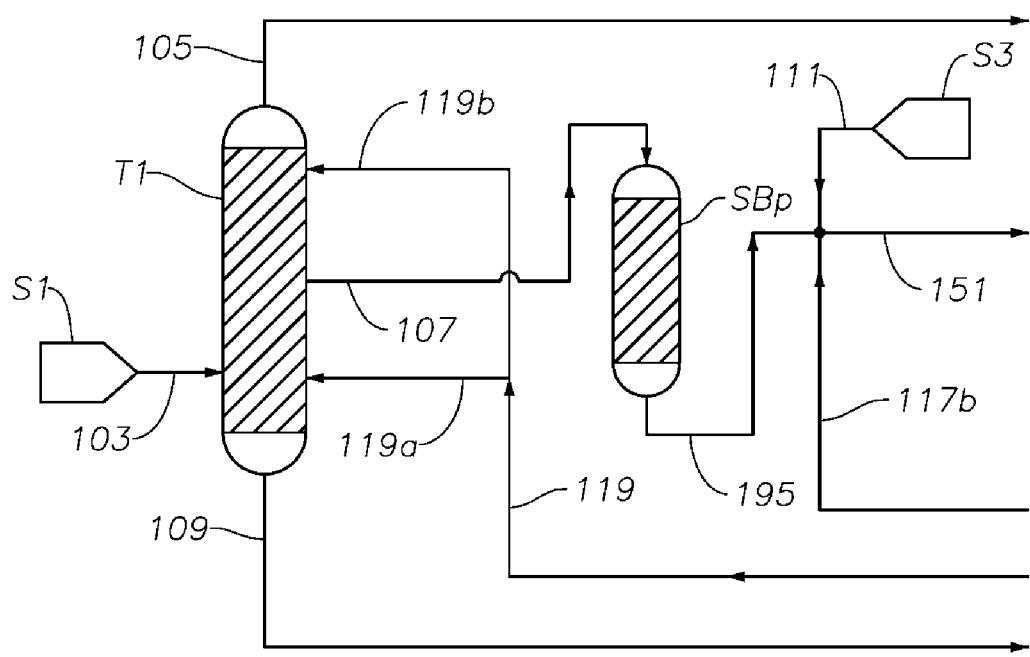
FIG. 8 is a schematic diagram showing a portion of a process/system similar to those shown in FIGS. 1 to 7, comprising a posterior sorbent bed SBp after the first distillation column T1 configured for removing at least a portion of the S-containing components from the phenol/cyclohexanone/cyclohexylbenzene feed fed to the hydrogenation reactor to reduce or prevent catalyst poisoning in the hydrogenation reactor.

FIG. 8 shows an alternative to the configuration of FIG. 7, and an example of one pre-hydrogenation treatment according to some embodiments. In this figure, instead of placing an anterior sorbent bed SBa before the first distillation column T1, a posterior sorbent bed SBp is placed behind column T1, which receives the first middle effluent 107 as a feed, produces a treated stream 195 depleted or low in S-containing components and/or any one or more other catalyst poison components such as light acids. A preferred posterior sorbent bed SBp comprises an Amberlyst® A26 ion exchange resin, referenced previously, although other sorbent beds, such as other ion exchange resins (e.g., Amberlyst® A21) may be used. The treated stream 195 is then delivered to the hydrogenation reactor as a portion or all of the hydrogenation feed 151 together with hydrogen feeds 111 and 117b. Alternatively, where the total concentration of the catalyst poison components (such as the S-containing components and/or other poisons) in the first middle effluent 107 is exceedingly high (and/or where concentrations of other impurities with different volatilities than phenol and cyclohexanone in the first middle effluent 107 are exceedingly high) a posterior distillation column (not shown) may be installed before or after (that is, upstream of or downstream of, respectively) the sorbent bed SBp, and effluent 107 may be treated by both the posterior distillation column and the posterior sorbent bed SBp before being fed to the hydrogenation reactor R1 as at least a portion of the hydrogenation feed. Such a posterior distillation column may be used to remove either light or heavy components relative to the phenol and cyclohexanone in the first middle effluent 107.

Further, other treatment options may be present instead of or in addition to the posterior distillation column (also not shown). For example, one or more additional posterior sorbent beds may be utilized, any one or more of which may be the same or different from the posterior sorbent bed SBp. Preferably, at least one additional posterior sorbent bed is different from the posterior sorbent bed SBp. For instance, a particularly suitable additional posterior sorbent bed comprises a nickel sorbent. Such a sorbent may remove S-containing components and/or other catalyst poison components from the effluent 107. It may also remove color bodies (e.g., trace byproducts that impart some degree of coloration to the effluent 107). Alternatively or in addition, at least one additional posterior sorbent bed may comprise an activated carbon sorbent. Desirably, upon treatment by one or more of (i) the posterior sorbent bed SBp, (ii) the posterior distillation column, and (iii) one or more additional posterior sorbent beds, concentrations of S-containing components capable of poisoning the hydrogenation catalyst are reduced significantly in the hydrogenation feed compared to in effluent 107. Preferably, concentrations of any other impurities, including other catalyst poison components and/or impurities having different volatilities from phenol and cyclohexanone, are also reduced. For instance, in the embodiment shown in FIG. 8 (employing a posterior sorbent bed SBp), the ratio of concentration of catalyst poison components (including S-containing components and other light components capable of poisoning the hydrogenation catalyst) in the effluent 107 to the concentration of said components in the hydrogenation feed is within the range of about 0.001 to 0.5, preferably about 0.001 to about 0.1, such as 0.001 to 0.1. For instance, the ratio of concentration of sulfuric acid in the hydrogenation feed to concentration of sulfuric acid in effluent 107 is preferably within the range of about 0.001 to about 0.1, such as 0.001 to 0.1. Furthermore, one or more additional pre-hydrogenation treatments (not shown) may be applied to stream 107, 195, and/or 151 (e.g., water and/or a chemical agent may be added to any of these streams, or a catalyst inhibitor may be temporarily delivered to the hydrogenation reactor through any one or more of these streams during initial start-up or re-start of the process).

If necessary, in some embodiments, both (i) the anterior treatment mechanism described in connection with FIG. 7 (e.g., one or both of the anterior distillation column and the anterior sorbent) and (ii) the posterior treatment mechanism described in connection with FIG. 8 (e.g., one or more of the posterior distillation column, the posterior sorbent bed, and the one or more additional posterior sorbent beds) may be used to prevent catalyst poison components (including the S-containing components) from entering into the hydrogenation reactor(s) at an unacceptably high concentration. The anterior and posterior sorbents, and/or the optional additional posterior sorbent(s), can be the same or different, and may each independently be selected from: massive nickel, activated carbon, ion exchange resins (such as strong and weak anion resins which are usually amine based), clay, kaolin, silica sorbents, alumina sorbents, molecular sieves, (i) oxides of alkali metals (e.g., Na), alkaline earth metals (e.g., Mg), and zinc; (ii) hydroxides of alkali metals (e.g., Na), alkaline earth metals (e.g., Mg), and zinc; (iii) carbonates of alkali metals (e.g., Na), alkaline earth metals (e.g., Mg), and zinc; (iv) bicarbonates of alkali metals (e.g., Na), alkaline earth metals (e.g., Mg), and zinc; (v) complexes of two or more of (i), (ii), (iii), and (iv); (vi) solid amines; (vii) ion-exchange resins; and (viii) mixtures and combinations of two or more of (i), (ii), (iii), (iv), (v), (vi), and (vii). The sorbents may remove impurities such as catalyst poison components (including the S-containing components) by physical absorption or adsorption, extraction, and/or chemical reactions. Massive nickel is particularly useful for removing S-containing and N-containing poison components. However, a basic, solid-phase sorbent material such as those described above is preferable for removing sulfuric acid. A basic ion exchange resin is particularly preferable for removing acid species and/or S-containing species.

Figure 9:
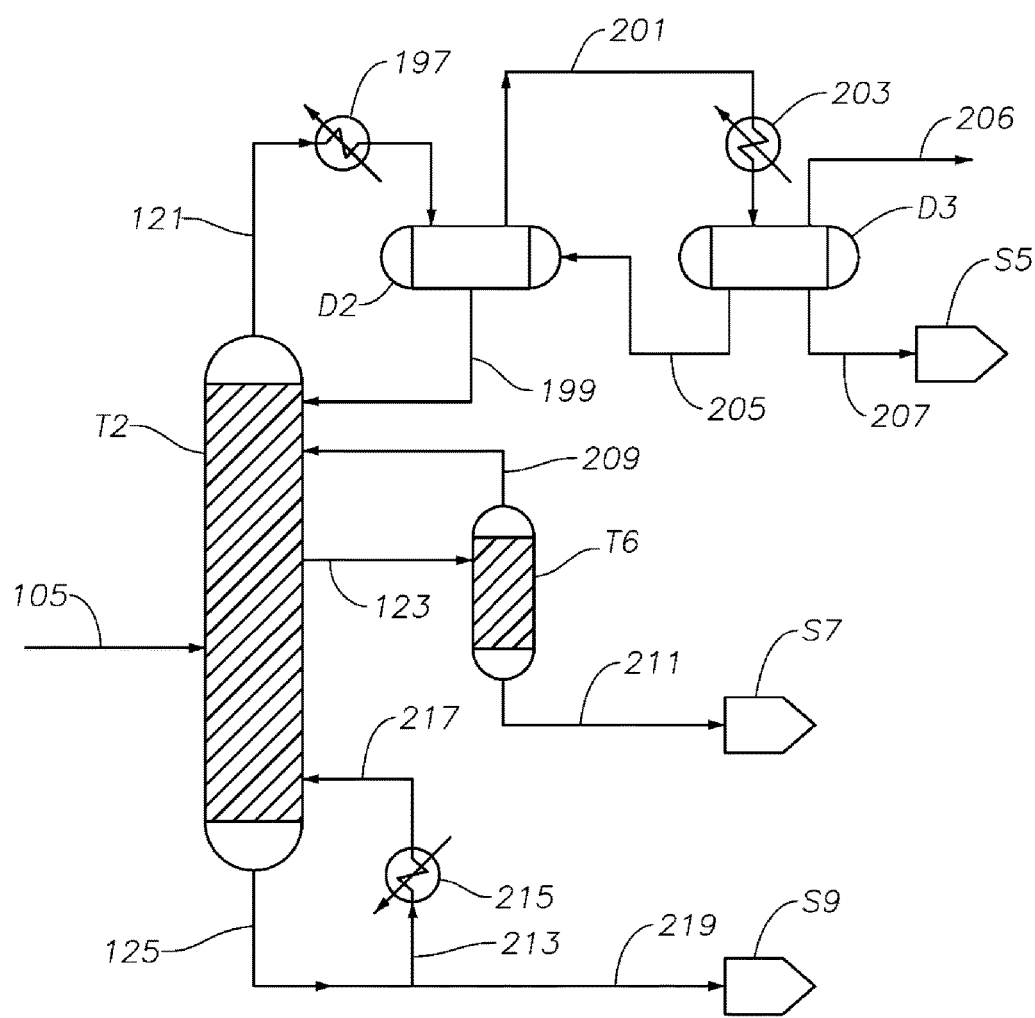
FIG. 9 is a schematic diagram showing a portion of a process/system similar to those shown in FIGS. 1 to 8, comprising a sorbent bed T6 after the cyclohexanone purification column T2, configured to reduce amounts of impurities (e.g., catalyst poison components) from the final cyclohexanone product.

FIG. 9 is a schematic diagram showing a portion of a process/system similar to those shown in FIGS. 1-8 comprising a side stripper column T6 after the cyclohexanone purification column T2, configured to reduce amounts of light components from the final cyclohexanone product. In this figure, the first upper effluent 105 comprising primarily cyclohexanone and light components obtained from the first distillation column T1 and from the upper anterior stripper effluent, if any, is delivered to cyclohexanone purification column T2, where three effluents are obtained: a second upper effluent 121 rich in light components such as water and methylcyclopentanone and depleted in cyclohexanone and cyclohexanol, a second middle effluent 123 rich in cyclohexanone and depleted in light components and cyclohexanol, and a second lower effluent 125 rich in cyclohexanol. Effluent 121 is first cooled down by a heat exchanger 197, then delivered to a separation drum D2 to obtain a liquid phase 199, which is recycled to column T2, and a vapor phase 201, which is cooled again by a heat exchanger 203, and delivered to another separation drum D3 to obtain a liquid phase which is partly recycled as stream 205 to drum D2, and partly delivered to storage S5, and a vapor phase 206 which can be purged. Effluent 123 is delivered to a side stripper T6 where the following streams are produced: a substantially pure cyclohexanone stream 211 in the vicinity of the bottom thereof, which is delivered to a storage S7; and a light component stream 209, which is recycled to the column T2 at a location above 123.

Additional post-hydrogenation treatment (e.g., of a phenol hydrogenation reaction effluent such as effluent 127 of FIG. 1) is also contemplated in some embodiments. For instance, similar to the embodiment of FIG. 9 (comprising further treatment by distillation and/or stripping of cyclohexanone from first distillation column T1), the product effluent from phenol hydrogenation (e.g., hydrogenation from reactor R1) may be subjected to one or more distillation procedures. Such additional distillation could take place in additional distillation columns, or could be effected by providing at least a portion of such phenol hydrogenation effluent to one or more of the first distillation column T1 or the cyclohexanone purification column T2 of the various embodiments just described. However, in any post-treatment of the cyclohexanone, particularly of a stream comprising the phenol hydrogenation reaction effluent, the stream should preferably not be subjected to temperatures in excess of 280° F. (137.8° C.), as it has been found that subjecting a phenol hydrogenation effluent to such temperatures may substantially increase the amount of cyclohexene present in the final product. Preferably, the product of any phenol hydrogenation is not subjected to temperatures in excess of 250° F. (121.1° C.), most preferably not in excess of 235° F. (112.8° C.), so as to minimize or avoid the formation of additional cyclohexene that could be present in the final product cyclohexanone composition. This includes operation of a distillation column such that temperature at or below the withdrawal point of a cyclohexanone-containing stream is in excess of the aforementioned temperatures, and further includes operation of a reboiler associated with any such distillation column, through which a product stream or a portion of a product stream may pass.

Cyclohexanone Compositions

In various embodiments, the methods and/or systems described herein create compositions that are rich in cyclohexanone (also referred to as cyclohexanone compositions).

Preferably, the cyclohexanone composition comprises at least 99 wt % cyclohexanone, based on the total weight of the cyclohexanone composition. More preferably, the cyclohexanone composition comprises at least 99.9 wt %, such as at least 99.94 wt %, 99.95, or even 99.99 wt % cyclohexanone.

The cyclohexanone composition may further comprise one or more cyclohexanone impurities selected from the following compounds: benzene, cyclohexene, pentanal, cyclopentanol, cyclohexanol, and phenol. As used herein, a "cyclohexanone impurity" is any compound other than cyclohexanone or water, which is typically acceptable in commercially available cyclohexanone compositions in small amounts. In the present invention, water is advantageously present in the cyclohexanone composition in amounts of 0.15 wt % or less, such as 0.1 wt % or less, or 0.05 wt % or less, based on total weight of the cyclohexanone composition. Preferably, the total amount of cyclohexanone impurities is 500 wppm or less, more preferably 200 wppm or less, most preferably 150 wppm or less, or even 100 wppm or less, each wppm being based upon the total weight of the cyclohexanone composition.

The cyclohexanone composition may comprise any one or more, two or more, three or more, or four or more of such cyclohexanone impurities. In particular embodiments, the cyclohexanone composition comprises one or both of pentanal and cyclopentanol. Compositions of such embodiments may also or instead comprise one or both of cyclohexene and cyclohexanol. The combined amount of cyclohexanone impurities in such embodiments is 200 wppm or less, preferably 100 wppm or less.

In certain embodiments, the cyclohexanone composition may consist of cyclohexanone, 0.15 wt % or less (preferably 0.1 wt % or less, most preferably 0.05 wt % or less) water, and 500 wppm or less (preferably 200 wppm or less, most preferably 100 wppm or less) of one or more cyclohexanone impurities. The cyclohexanone impurities in such embodiments are preferably selected from the group consisting of: benzene, cyclohexene, pentanal, cyclopentanol, cyclohexanol, and phenol. In certain embodiments, the cyclohexanone impurities are selected from the group consisting of: cyclohexene, pentanal, cyclopentanol, and cyclohexanol. Such compositions may consist of any one, two, three, or four of the foregoing impurities. In particular embodiments, the impurities consist of cyclohexene, pentanal, cyclopentanol, and cyclohexanol. In yet further particular embodiments, the impurities consist of (i) cyclohexene, (ii) cyclopentanol or pentanal, and (iii) cyclohexanol.

With respect to each aforementioned cyclohexanone impurity in the cyclohexanone compositions of various embodiments:

Benzene may be present in an amount ranging from 0 to 20 wppm. For instance, benzene may be present at 0 wppm to 5 wppm, preferably 0 wppm to 2.5 wppm.

Cyclohexene may be present in an amount ranging from 0 to 20 wppm. For instance, cyclohexene may be present at 0 wppm to 15 wppm, such as 2.5 wppm to 15, or 5 wppm to 10 wppm.

Pentanal may be present in an amount ranging from 0 to 20 wppm, provided the high end of the range is greater than the low end. For instance, pentanal may be present at 0 wppm to 10 wppm, such as 1 wppm to 10 wppm, potentially 3 wppm to 7 wppm.

Cyclopentanol may be present in an amount ranging from 0 to 80 wppm. For instance, cyclopentanol may be present at 10 wppm to 50 wppm, such as 15 to 40 wppm, or 20 to 35 wppm.

Cyclohexanol may be present in an amount ranging from 0 to 80 wppm. For instance, cyclohexanol may be present at 0 wppm to 40 wppm, such as 10 wppm to 40 wppm, for instance 12 wppm to 30 wppm, or 10 wppm to 20 wppm.

In various embodiments, any one or more of these cyclohexanone impurities may have been generated in situ during a process for making cyclohexanone (i.e., they were not added from an external source). For instance, any one or more of the cyclohexanone impurities may have been formed during the phenol hydrogenation reaction. This is particularly likely for cyclohexanone impurities such as cyclohexanol, cyclohexene, and water. Additionally, any trace amount of unreacted phenol left over from the hydrogenation reaction may remain as a cyclohexanone impurity in some embodiments. Furthermore, in certain embodiments, at least a portion of the cyclohexene may have been produced at least in part during distillation or other treatment of all or part of the phenol hydrogenation reaction effluent (i.e., the products of hydrogenation of the hydrogenation feed comprising cyclohexanone and phenol, such as takes place in R1 of FIG. 1). As already noted, however, such amounts of cyclohexene may be minimized by avoiding subjecting said all or part of the phenol hydrogenation reaction effluent to temperatures in excess of 280° F., preferably avoiding temperatures in excess of 250° F., most preferably avoiding temperatures in excess of 235° F.

Further, in various embodiments, all or at least part of the pentanal and/or cyclopentanol may be formed either before or after (i.e., upstream or downstream of, respectively) hydrogenation of the hydrogenation feed comprising cyclohexanone and phenol. For instance, in some embodiments in accordance with FIGS. 1, 7, and/or 8, pentanal and/or cyclopentanol may be formed in the first distillation column T1. In yet other embodiments in accordance with FIGS. 7 and/or 8, pentanal and/or cyclopentanol may be formed in a posterior distillation column and/or an anterior distillation column used to pre-treat hydrogenation reaction feed. In yet further embodiments, pentanal and/or cyclopentanol may be formed in any distillation column or other treatment to which all or a portion of the phenol hydrogenation reaction effluent is subjected.

Uses of Cyclohexanone and Phenol

The cyclohexanone composition produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6. Thus, further embodiments may include caprolactam produced using a cyclohexanone composition according to any of the aforementioned embodiments. Likewise, further embodiments may include nylon produced using a cyclohexanone composition according to any of the aforementioned embodiments. Similarly, methods according to some embodiments may include producing one or both of caprolactam and nylon using a cyclohexanone composition according to any of the aforementioned embodiments.

The phenol produced through the processes disclosed herein may be used, for example, to produce phenolic resins, bisphenol A, ε-caprolactam, adipic acid, and/or plasticizers.

EXAMPLES

Some aspects of the above-described embodiments are further illustrated through the non-limiting examples below.

Example 1

150 g of a hydrogenation feed (70 wt % phenol, 25 wt % cyclohexanone, 5 wt % cyclohexylbenzene) was charged along with 0.5 g hydrogenation catalyst (Pd on activated carbon support in powder form) to a 300-mL Parr autoclave which had been purged with nitrogen three times. The autoclave was pressurized with hydrogen to 70 psig (482.6 kPa), and the contents of the autoclave heated to 150° C. with stirring (1000 rpm). Three runs of the reaction were conducted using the above procedures and conditions, with the only differences being: in Run 1, no $Na_2CO_3$ was added to the hydrogenation feed charged to the autoclave; in Run 2, 0.06 g $Na_2CO_3$ was charged to the autoclave with the hydrogenation feed (about 0.04 wt % on the basis of hydrogenation feed); and in Run 3, 0.12 g $Na_2CO_3$ was charged to the autoclave with the hydrogenation feed (about 0.08 wt % on the basis of hydrogenation feed).

Figure 11:
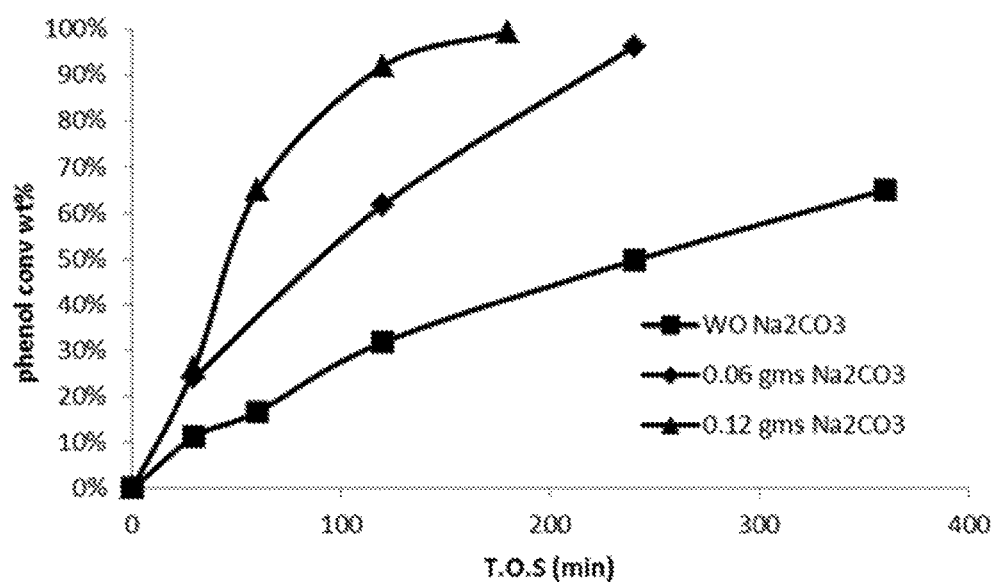
FIG. 11 is a plot of phenol conversion as a function of time on stream for various experimental reactions carried out according to the procedure described in Example 1.
Figure 12:
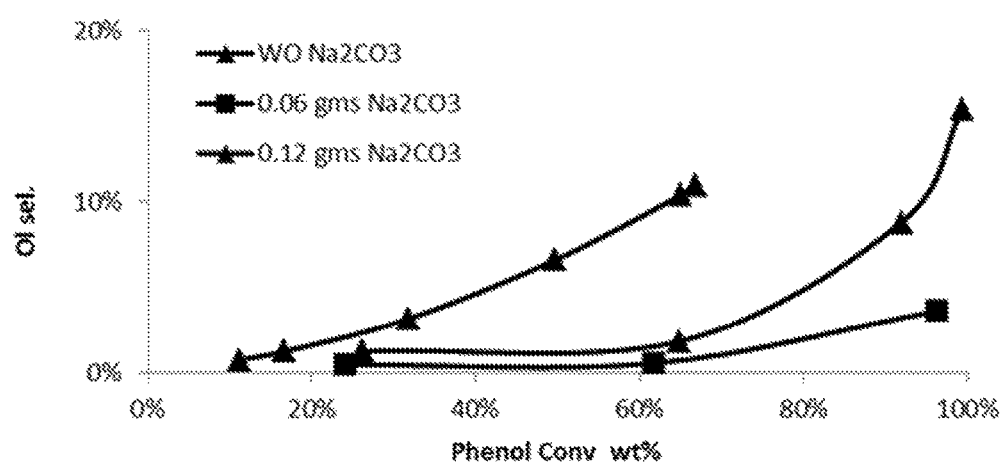
FIG. 12 is a plot of cyclohexanol selectivity as a function of phenol conversion for various experimental reactions carried out according to the procedure described in Example 1.
Figure 13:
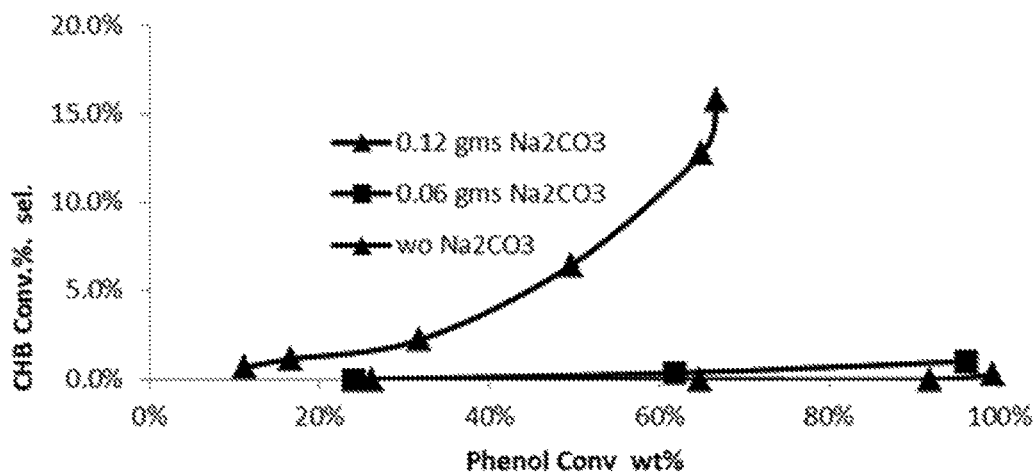
FIG. 13 is a plot of cyclohexylbenzene conversion as a function of phenol conversion for various experimental reactions carried out according to the procedure described in Example 1.

Phenol conversion was plotted against time on stream to demonstrate the rate of conversion in each run, shown in FIG. 11. Cyclohexanol selectivity was plotted against phenol conversion for each run, shown in FIG. 12. Finally, cyclohexylbenzene conversion was also plotted against phenol conversion, shown in FIG. 13.

The results demonstrate that addition of $Na_2CO_3$ not only sped up the conversion of phenol, but furthermore lowered the cyclohexanol selectivity and suppressed the undesired cyclohexylbenzene hydrogenation side reaction.

Example 2

Once again, 150 g of a hydrogenation feed (70 wt % phenol, 25 wt % cyclohexanone, 5 wt % cyclohexylbenzene) was charged along with 0.5 g hydrogenation catalyst (Pd on activated carbon support in powder form) to a 300-mL Parr autoclave which had been purged with nitrogen three times. The autoclave was pressurized with hydrogen to 70 psig (482.6 kPa), and the contents of the autoclave heated to 150° C. with stirring (1000 rpm).

Figure 14:
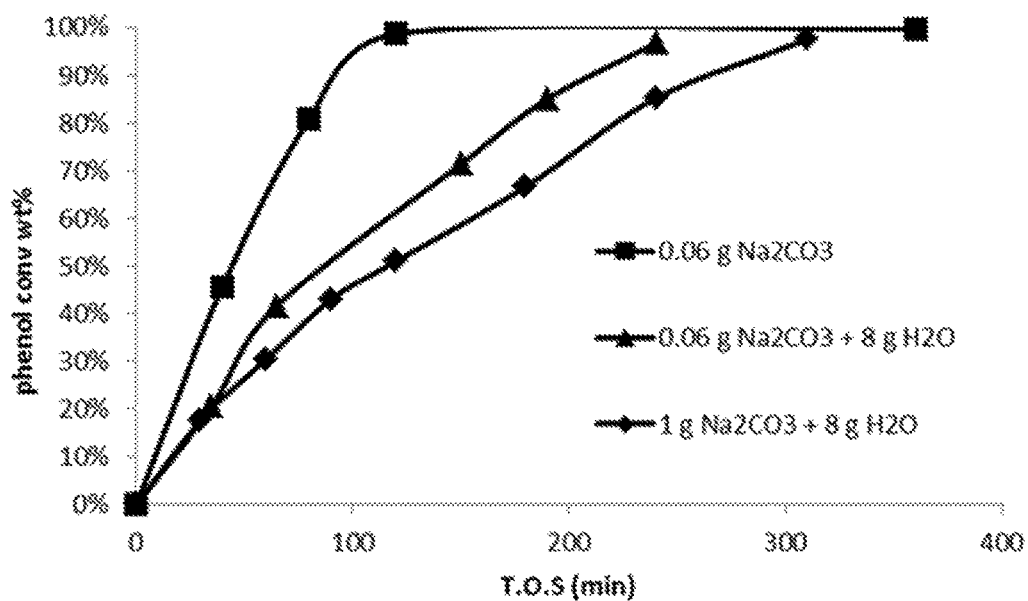
FIG. 14 is a plot of phenol conversion as a function of time on stream for various experimental reactions carried out according to the procedure described in Example 2.
Figure 15:
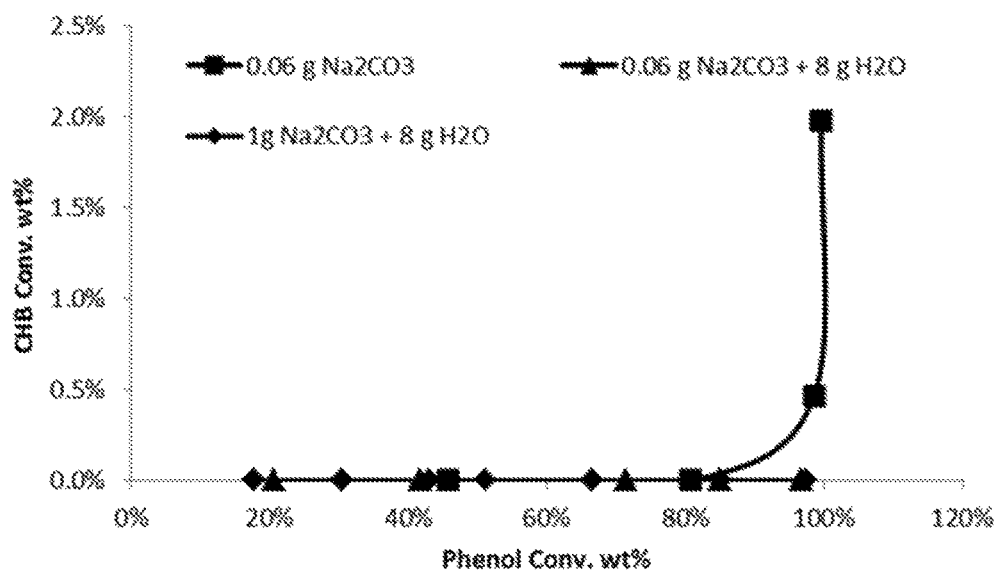
FIG. 15 is a plot of cyclohexylbenzene conversion as a function of phenol conversion for various experimental reactions carried out according to the procedure described in Example 2.

Three runs of the reaction were conducted using the above procedures and conditions, with the only difference being: in Run 1, 0.06 g $Na_2CO_3$ (about 0.04 wt % on the basis of hydrogenation feed) were added to hydrogenation feed; in Run 2, 0.06 g $Na_2CO_3$ and 8 g $H_2O$ were added to the hydrogenation feed; and in Run 3, 1 g $Na_2CO_3$ and 8 g $H_2O$ were added to the hydrogenation feed. FIG. 14 shows the phenol conversion as a function of time on stream for each run, and FIG. 15 shows cyclohexylbenzene conversion as a function of phenol conversion. Although the addition of water in Runs 2 and 3 slowed the rate of phenol conversion, water completely inhibited the undesired cyclohexylbenzene hydrogenation side reaction. It is hypothesized that water formed a small hydrophilic layer around the hydrogenation catalyst, through which phenol could diffuse but cyclohexylbenzene could not, therefore preventing the catalyzed hydrogenation of cyclohexylbenzene.

Example 3

A laboratory-scale continuous hydrogenation reaction was carried out over a Pd-on-alumina hydrogenation catalyst commercially available from BASF SE, comprising 1 wt % Na dopant. The feed comprised a crude phenol/cyclohexanone mixture produced by hydroalkylation of benzene to cyclohexylbenzene, oxidation of the resulting cyclohexylbenzene to cyclohexylbenzene-hydroperoxide, and cleavage to a cleavage reaction product comprising cyclohexanone and phenol, as described above in connection with various embodiments. To the feed was added 12 wt % water (on the basis of phenol in the feed). The continuous reaction was carried out in the vapor phase in a shell-and-tubes heat exchange reactor (10 psig (68.9 kPag), 3.5 $hr^{-1}$ WHSV, 4:1 hydrogen-to-phenol molar ratio). Temperature was initially held constant at 180° C. for the first 300 g of phenol in the feed per g catalyst in the reactor, then lowered to 165° C., as shown in FIGS. 16 and 17.

Figure 16:
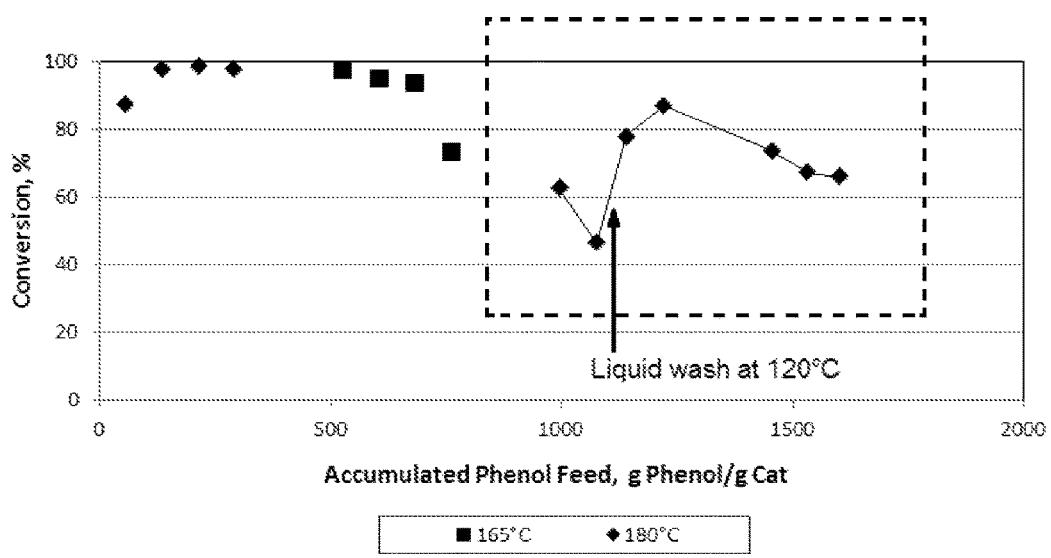
FIG. 16 is a plot of phenol conversion as a function of accumulated phenol feed (g phenol per g catalyst) in an experimental reaction carried out according to the procedure described in Example 3.
Figure 17:
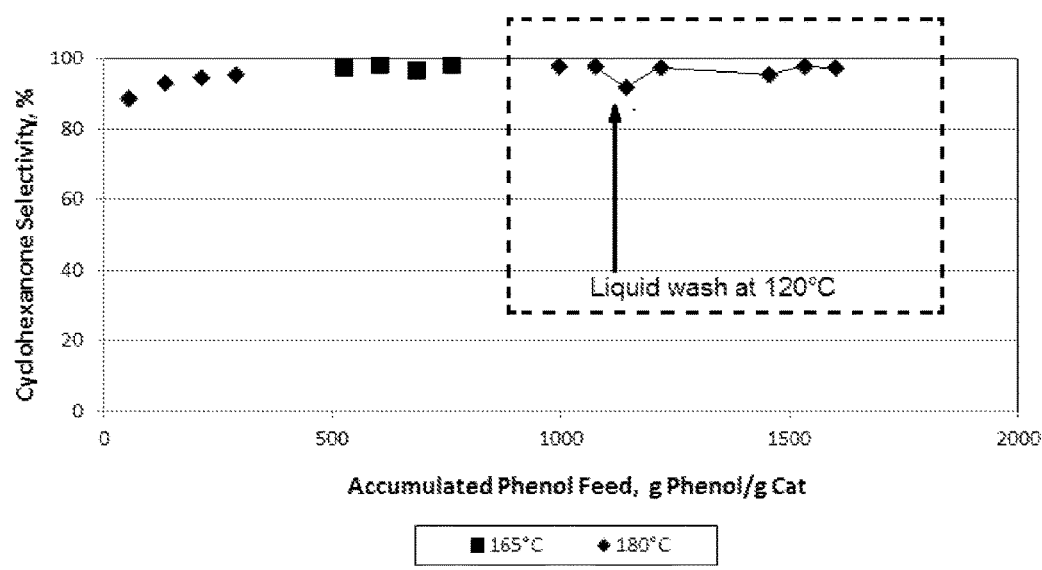
FIG. 17 is a plot of cyclohexanone selectivity as a function of accumulated phenol feed (g phenol per g catalyst) in an experimental reaction carried out according to the procedure described in Example 3.

FIG. 16 shows the phenol conversion as a function of accumulated phenol feed (g phenol/g catalyst), and FIG. 17 shows the selectivity to cyclohexanone as a function of accumulated phenol feed. As shown in FIGS. 16 and 17, after approximately 1000 g phenol fed per g catalyst, conversion had declined sharply (from a peak of around 99% to just over 60%), and after approximately 1100 g phenol fed per g catalyst, cyclohexanone selectivity had fallen to around 90% from a high of 99%. FIGS. 16 and 17 also show the point of time at which hydrogenation reaction conditions were adjusted to 120° C. at 10 psig (68.9 kPag), putting the reaction into mixed-phase, thereby enabling liquid stripping of the catalyst according to some embodiments. As shown in FIG. 16, the liquid stripping restored a substantial portion of catalyst activity (bringing phenol conversion back up to around 80%). As shown in FIG. 17, the liquid stripping also returned cyclohexanone selectivity back to around 99%. The experiment indicates that liquid stripping is an effective means of restoring catalyst activity while continuing the hydrogenation reaction.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The invention claimed is:

1. A process comprising:
    (a-1) during a first period of time, continuously providing hydrogen and hydrogenation feed comprising phenol, cyclohexanone, and cyclohexylbenzene to a hydrogenation reaction zone in which a hydrogenation catalyst bed is disposed, thereby maintaining a reaction medium flowing through the hydrogenation catalyst bed within the hydrogenation reaction zone;
    (a-2) during the first period of time, maintaining initial temperature and initial pressure conditions within the hydrogenation reaction zone such that the reaction medium is entirely in vapor phase during the first period of time;
    (b) adjusting the initial temperature conditions, the initial pressure conditions, or both, within the hydrogenation reaction zone to obtain liquid washing temperature and pressure conditions within the hydrogenation reaction zone, such that the reaction medium is in mixed liquid and vapor phase after the adjusting; and
    (c) during a second period of time subsequent to the first period of time, maintaining the liquid washing temperature and pressure conditions within the hydrogenation reaction zone while continuously providing the hydrogen and the hydrogenation feed to the hydrogenation reaction zone, thereby maintaining the reaction medium flowing through the hydrogenation catalyst bed in mixed liquid and vapor phase.

2. The process of claim 1, further comprising:
    (d) adjusting the liquid washing temperature conditions, the liquid washing pressure conditions, or both, so as to return to the initial temperature and pressure conditions within the hydrogenation reaction zone; and
    (e) during a third period of time subsequent to the second period of time, maintaining the initial temperature and pressure conditions within the hydrogenation reaction zone while continuously providing the hydrogen and the hydrogenation feed to the hydrogenation reaction zone, thereby maintaining the reaction medium flowing through the hydrogenation catalyst bed entirely in vapor phase.

3. The process of claim 1, wherein the initial temperature and pressure conditions comprise temperature within the range of 140° C. to 300° C. and pressure within the range of 0 kPag to 2000 kPag; and further wherein the liquid washing temperature and pressure conditions comprise temperature within the range of 25° C. to 250° C. and pressure within the range of 0 kPag to 2000 kPag.

4. The process of claim 1, wherein, during at least a portion of the second period of time, liquid holdup within the hydrogenation reaction zone is maintained at greater than or equal to 1 vol %, based upon the available void volume in the hydrogenation catalyst bed.

5. The process of claim 1, wherein, during at least a portion of the second period of time, liquid mass flux through the hydrogenation catalyst bed is at least 2 kg/m²s.

6. The process of claim 1, wherein the hydrogenation reaction zone comprises a shell-and-tubes heat exchange reactor, and further wherein the hydrogenation catalyst bed is disposed within one or more tubes of the shell-and-tubes heat exchange reactor.

7. The process of claim 6, wherein the adjusting (b) comprises adjusting the temperature, the flow rate, or both, of a heat exchange fluid flowing through the shell and around the tubes of the shell-and-tubes heat exchange reactor.

8. The process of claim 1, wherein the hydrogenation catalyst bed's activity declines during the first period of time, and further wherein the adjusting (b) and the maintaining (c) restore at least a portion of the activity of the hydrogenation catalyst bed.

9. The process of claim 1, wherein the hydrogenation feed continuously provided to the hydrogenation reaction zone during the first and second time periods is obtained from cleavage reaction product, and further wherein the cleavage reaction product is obtained from a process comprising:
    (1) hydroalkylating benzene and hydrogen to obtain cyclohexylbenzene;
    (2) oxidizing at least a portion of the cyclohexylbenzene to obtain cyclohexylbenzene-hydroperoxide; and
    (3) cleaving at least a portion of the cyclohexylbenzene-hydroperoxide to obtain the cleavage reaction product comprising phenol, cyclohexanone, and cyclohexylbenzene.

10. The process of claim 9, wherein the hydrogenation feed, prior to being continuously provided to the hydrogenation reaction zone, has been subjected to one or more pre-hydrogenation treatments selected from the group consisting of: (i) contacting the hydrogenation feed with one or more posterior sorbents; (ii) contacting the hydrogenation feed with one or more posterior distillation columns; (iii) adding to the hydrogenation feed a basic chemical agent selected from the group consisting of amines, inorganic bases, and mixtures thereof; and (iv) adding water to the hydrogenation feed such that, upon being provided to the hydrogenation reaction zone, water is present in the hydrogenation feed in an amount ranging from 0.1 wt % to 20 wt %, based on the weight of the hydrogenation feed.

11. A process comprising:
    (a) during a first period of time, flowing (i) hydrogen and (ii) a vapor-phase hydrogenation feed comprising phenol, cyclohexanone, and cyclohexylbenzene through a hydrogenation catalyst bed so as to hydrogenate at least a portion of the phenol in the vapor-phase hydrogenation feed to cyclohexanone, and further so as to form one or more hydrocarbon and/or oxygenate impurities that adsorb or absorb onto at least a portion of the hydrogenation catalyst bed; and
    (b) during a second period of time subsequent to the first period of time, flowing (i) hydrogen and (ii) a mixed liquid- and vapor-phase hydrogenation feed comprising phenol, cyclohexanone, and cyclohexylbenzene through the hydrogenation catalyst bed so as to hydrogenate at least a portion of the phenol in the mixed liquid- and vapor-phase hydrogenation feed to cyclohexanone, and further so as to remove at least a portion of the one or more hydrocarbon and/or oxygenate impurities from the hydrogenation catalyst bed.

12. The process of claim 11, further comprising:
(c) during a third period of time subsequent to the second period of time, flowing (i) hydrogen and (ii) additional vapor-phase hydrogenation feed comprising phenol, cyclohexanone, and cyclohexylbenzene through a hydrogenation catalyst bed so as to hydrogenate at least a portion of the phenol in the additional vapor-phase hydrogenation feed to cyclohexanone.

13. The process of claim 11, wherein both the vapor-phase hydrogenation feed and the mixed liquid- and vapor-phase hydrogenation feed are provided to a hydrogenation reaction zone in which the hydrogenation catalyst bed is disposed, and further wherein:
   (a-1) during the first period of time, the temperature in the hydrogenation reaction zone is maintained within the range of 100° C. to 300° C., and the pressure in the hydrogenation reaction zone is maintained within the range of 0 kPag to 2000 kPag; and
   (b-1) during the second period of time, the temperature in the hydrogenation reaction zone is maintained within the range of 25° C. to 250° C., and the pressure in the hydrogenation reaction zone is maintained within the range of 0 kPag to 2000 kPag.

14. The process of claim 11, wherein, during at least a portion of the second period of time, liquid mass flux through the hydrogenation catalyst bed is at least 2 kg/m²s.

15. The process of claim 13, wherein, during at least a portion of the second period of time, liquid holdup within the hydrogenation reaction zone is maintained at greater than or equal to 1 vol %, based upon the available void volume in the hydrogenation catalyst bed.

16. The process of claim 13, wherein the hydrogenation reaction zone comprises a shell-and-tubes heat exchange reactor, and further wherein the hydrogenation catalyst bed is disposed within one or more tubes of the shell-and-tubes heat exchange reactor.

17. The process of claim 11, wherein the formation of the one or more hydrocarbon and/or oxygenate impurities decreases activity of the hydrogenation catalyst bed; and further wherein removal of at least a portion of the hydrocarbon and/or oxygenate impurities from the hydrogenation catalyst bed restores at least a portion of the hydrogenation catalyst bed's activity.

18. The process of claim 11, wherein the vapor-phase hydrogenation feed and the mixed liquid- and vapor-phase hydrogenation feed are obtained from a cleavage reaction product, wherein the cleavage reaction product is obtained from a process comprising:
   (1) hydroalkylating benzene and hydrogen to obtain cyclohexylbenzene;
   (2) oxidizing at least a portion of the cyclohexylbenzene to obtain cyclohexylbenzene-hydroperoxide; and
   (3) cleaving at least a portion of the cyclohexylbenzene-hydroperoxide to obtain the cleavage reaction product comprising phenol, cyclohexanone, and cyclohexylbenzene.

19. The process of claim 18, wherein, prior to being flowed through the hydrogenation catalyst bed, each of the vapor-phase hydrogenation feed and the mixed liquid- and vapor-phase hydrogenation feed has been subjected to one or more pre-hydrogenation treatments selected from the group consisting of: (i) contacting the hydrogenation feed with one or more posterior sorbents; (ii) contacting the hydrogenation feed with one or more posterior distillation columns; (iii) adding to the hydrogenation feed a basic chemical agent selected from the group consisting of amines, inorganic bases, and mixtures thereof; and (iv) adding water to the hydrogenation feed such that, upon being provided to the hydrogenation reaction zone, water is present in the hydrogenation feed in an amount ranging from 0.1 wt % to 20 wt %, based on the weight of the hydrogenation feed.

* * * * *